(12) United States Patent
Takahashi et al.

(10) Patent No.: US 7,371,541 B2
(45) Date of Patent: May 13, 2008

(54) G PROTEINS, POLYNUCLEOTIDE ENCODING THE SAME AND UTILIZATION THEREOF

(75) Inventors: Yasuhiko Takahashi, Toyonaka (JP);
Yasuo Matsumoto, Toyonaka (JP);
Kenji Oeda, Kyoto (JP)

(73) Assignee: Sumitomo Chemical Company, Limited, Osaka (JP)

( * ) Notice: Subject to any disclaimer, the term of this patent is extended or adjusted under 35 U.S.C. 154(b) by 489 days.

(21) Appl. No.: 10/618,320

(22) Filed: Jul. 11, 2003

(65) Prior Publication Data

US 2005/0260595 A1    Nov. 24, 2005

(30) Foreign Application Priority Data

Jul. 16, 2002  (JP) .............................. 2002-206841
Dec. 19, 2002  (JP) .............................. 2002-367778
Mar. 31, 2003  (JP) .............................. 2003-095955

(51) Int. Cl.
*C07K 14/47*   (2006.01)
*C12N 15/12*   (2006.01)
*G01N 33/566*  (2006.01)

(52) U.S. Cl. ..................... 435/69.1; 435/7.1; 435/7.2; 435/252.3; 435/320.1; 530/350; 536/23.5

(58) Field of Classification Search ..................... None
See application file for complete search history.

(56) References Cited

U.S. PATENT DOCUMENTS 5,194,596 A * 3/1993 Tischer et al. .............. 530/399
5,350,836 A * 9/1994 Kopchick et al. ........... 530/399

FOREIGN PATENT DOCUMENTS

JP    WO 2005/047318 A1   5/2005
WO    WO 01/75067         10/2001
WO    WO 02/22882 A2      3/2002
WO    WO 03/016475        2/2003

OTHER PUBLICATIONS

Skolnick et al., Trends in Biotech., 18(1):34-39, 2000.*
Vukicevic et al., 1996, PNAS USA 93:9021-9026.*
Choh, PNAS 77(6):3211-14, 1990.*
Accession No. L10665, direct submission Feb. 16, 1993.
Accession No. AAH48980, direct submission Mar. 17, 2003.
Bourne, H., The GTPase superfamily: conserved structure and molecular mechanism, Nature, vol. 349, pp. 117-127, 1991.
Jones, D.T., et al., Golf: An olfactory neuron specific-G protein involved in odorant signal transduction, Science, American Association for the Advancement of Science, US, vol. 224, No. 4906, May 19, 1989 pp. 790-795, XP-001109598.
Zigman, J.M., et al., Human Golf alpha: conplementary deoxyribonucleic acid structure and expression in pancreatic islets and other tissues outside the olfactory neuroepithelium and central nervous system, Endocrinology, Baltimore, MD, US, vol. 133, No. 8, Dec. 1993, pp. 2508-2514, XP-000993079.

* cited by examiner

*Primary Examiner*—John Ulm
(74) *Attorney, Agent, or Firm*—Panitch Schwarze Belisario & Nadel LLP

(57) ABSTRACT

We identified a novel protein (Gm1) comprising an amino acid sequence part having a high homology with a domain having a high homology with a GTP binding site and a GTPase site conserved among G protein α subunits and a trimer forming domain conserved among G protein α subunits. The Gm1 is involved in an signal transduction via a G protein-coupled receptor (GPCR) stimulation. Accordingly, this protein is considered to be a novel G protein. The Gm1 is expressed intensively in human brain, thymus, testes, spleen, small intestine, uterus and heart. We also established a method for screening for a substance capable of regulating a cellular signal transduction employing a polynucleotide encoding the Gm1.

19 Claims, 4 Drawing Sheets

SEQUENCE LISTING

```
<160> NUMBER OF SEQ ID NOS: 34

<210> SEQ ID NO 1
<211> LENGTH: 458
<212> TYPE: PRT
<213> ORGANISM: Homo sapiens

<400> SEQUENCE: 1

Met Gly Leu Cys Tyr Ser Leu Arg Pro Leu Leu Phe Gly Gly Pro Gly
 1               5                  10                  15

Asp Asp Pro Cys Ala Ala Ser Glu Pro Val Glu Asp Ala Gln Pro
            20                  25                  30

Ala Pro Ala Pro Ala Leu Ala Pro Val Arg Ala Ala Ala Arg Asp Thr
        35                  40                  45

Ala Arg Thr Leu Leu Pro Arg Gly Gly Glu Gly Ser Pro Ala Cys Ala
    50                  55                  60

Arg Pro Lys Ala Asp Lys Pro Lys Glu Lys Arg Gln Arg Thr Glu Gln
65                  70                  75                  80

Leu Ser Ala Glu Glu Arg Glu Ala Ala Lys Glu Arg Glu Ala Val Lys
                85                  90                  95
```

```
Glu Ala Arg Lys Val Ser Arg Gly Ile Asp Arg Met Leu Arg Asp Gln
            100                 105                 110

Lys Arg Asp Leu Gln Gln Thr His Arg Leu Leu Leu Gly Ala Gly
        115                 120                 125

Glu Ser Gly Lys Ser Thr Ile Val Lys Gln Met Arg Ile Leu His Val
130                 135                 140

Asn Gly Phe Asn Pro Glu Glu Lys Lys Gln Lys Ile Leu Asp Ile Arg
145                 150                 155                 160

Lys Asn Val Lys Asp Ala Ile Val Thr Ile Val Ser Ala Met Ser Thr
                165                 170                 175

Ile Ile Pro Pro Val Pro Leu Ala Asn Pro Glu Asn Gln Phe Arg Ser
            180                 185                 190

Asp Tyr Ile Lys Ser Ile Ala Pro Ile Thr Asp Phe Glu Tyr Ser Gln
        195                 200                 205

Glu Phe Phe Asp His Val Lys Lys Leu Trp Asp Asp Glu Gly Val Lys
210                 215                 220

Ala Cys Phe Glu Arg Ser Asn Glu Tyr Gln Leu Ile Asp Cys Ala Gln
225                 230                 235                 240

Tyr Phe Leu Glu Arg Ile Asp Ser Val Ser Leu Val Asp Tyr Thr Pro
                245                 250                 255

Thr Asp Gln Asp Leu Leu Arg Cys Arg Val Leu Thr Ser Gly Ile Phe
            260                 265                 270

Glu Thr Arg Phe Gln Val Asp Lys Val Asn Phe His Met Phe Asp Val
        275                 280                 285

Gly Gly Gln Arg Asp Glu Arg Arg Lys Trp Ile Gln Cys Phe Asn Asp
290                 295                 300

Val Thr Ala Ile Ile Tyr Val Ala Ala Cys Ser Ser Tyr Asn Met Val
305                 310                 315                 320

Ile Arg Glu Asp Asn Asn Thr Asn Arg Leu Arg Glu Ser Leu Asp Leu
                325                 330                 335

Phe Glu Ser Ile Trp Asn Asn Arg Trp Leu Arg Thr Ile Ser Ile Ile
            340                 345                 350

Leu Phe Leu Asn Lys Gln Asp Met Leu Ala Glu Lys Val Leu Ala Gly
        355                 360                 365

Lys Ser Lys Ile Glu Asp Tyr Phe Pro Glu Tyr Ala Asn Tyr Thr Val
370                 375                 380

Pro Glu Asp Ala Thr Pro Asp Ala Gly Glu Asp Pro Lys Val Thr Arg
385                 390                 395                 400

Ala Lys Phe Phe Ile Arg Asp Leu Phe Leu Arg Ile Ser Thr Ala Thr
                405                 410                 415

Gly Asp Gly Lys His Tyr Cys Tyr Pro His Phe Thr Cys Ala Val Asp
            420                 425                 430

Thr Glu Asn Ile Arg Arg Val Phe Asn Asp Cys Arg Asp Ile Ile Gln
        435                 440                 445

Arg Met His Leu Lys Gln Tyr Glu Leu Leu
    450                 455

<210> SEQ ID NO 2
<211> LENGTH: 1377
<212> TYPE: DNA
<213> ORGANISM: Homo sapiens
<220> FEATURE:
<221> NAME/KEY: CDS
<222> LOCATION: (1)..(1377)
```

-continued

<400> SEQUENCE: 2

```
atg ggt ctg tgc tac agt ctg cgg ccg ctg ctt ttc ggg ggc cca ggg      48
Met Gly Leu Cys Tyr Ser Leu Arg Pro Leu Phe Gly Gly Pro Gly
 1               5                  10                  15 gac gac ccc tgc gcg gcc tcg gag ccg ccg gtg gag gac gcg cag ccc      96
Asp Asp Pro Cys Ala Ala Ser Glu Pro Pro Val Glu Asp Ala Gln Pro
             20                  25                  30 gcc ccg gcc ccg gcc ctg gcc cca gtc cgg gcg gcc gca agg gac acg     144
Ala Pro Ala Pro Ala Leu Ala Pro Val Arg Ala Ala Ala Arg Asp Thr
         35                  40                  45 gcc cgg acc ctg ctc cct cgg ggc ggc gaa ggg agc ccg gca tgc gct     192
Ala Arg Thr Leu Leu Pro Arg Gly Gly Glu Gly Ser Pro Ala Cys Ala
 50                  55                  60 cgg ccc aaa gca gac aag ccg aag gag aag cgg cag cgc acc gag cag     240
Arg Pro Lys Ala Asp Lys Pro Lys Glu Lys Arg Gln Arg Thr Glu Gln
 65                  70                  75                  80 ctg agt gcc gag gag cgc gag gcg gcc aag gag cgc gag gcg gtc aag     288
Leu Ser Ala Glu Glu Arg Glu Ala Ala Lys Glu Arg Glu Ala Val Lys
                 85                  90                  95 gag gcg agg aaa gtg agc cgg ggc atc gac cgc atg ctg cgc gac cag     336
Glu Ala Arg Lys Val Ser Arg Gly Ile Asp Arg Met Leu Arg Asp Gln
            100                 105                 110 aag cgc gac ctg cag cag acg cac cgg ctc ctg ctc ctc ggg gct ggt     384
Lys Arg Asp Leu Gln Gln Thr His Arg Leu Leu Leu Leu Gly Ala Gly
        115                 120                 125 gag tct ggg aaa agc acc atc gtc aaa cag atg agg atc ctg cac gtc     432
Glu Ser Gly Lys Ser Thr Ile Val Lys Gln Met Arg Ile Leu His Val
    130                 135                 140 aat ggg ttt aat ccc gag gaa aag aaa cag aaa att ctg gac atc cgg     480
Asn Gly Phe Asn Pro Glu Glu Lys Lys Gln Lys Ile Leu Asp Ile Arg
145                 150                 155                 160 aaa aat gtt aaa gat gct atc gtg aca att gtt tca gca atg agt act     528
Lys Asn Val Lys Asp Ala Ile Val Thr Ile Val Ser Ala Met Ser Thr
                165                 170                 175 ata ata cct cca gtt ccg ctg gcc aac cct gaa aac caa ttt cga tca     576
Ile Ile Pro Pro Val Pro Leu Ala Asn Pro Glu Asn Gln Phe Arg Ser
            180                 185                 190 gac tac atc aag agc ata gcc cct atc act gac ttt gaa tat tcc cag     624
Asp Tyr Ile Lys Ser Ile Ala Pro Ile Thr Asp Phe Glu Tyr Ser Gln
        195                 200                 205 gaa ttc ttt gac cat gtg aaa aaa ctt tgg gac gat gaa ggc gtg aag     672
Glu Phe Phe Asp His Val Lys Lys Leu Trp Asp Asp Glu Gly Val Lys
    210                 215                 220 gca tgc ttt gag aga tcc aac gaa tac cag ctg att gac tgt gca caa     720
Ala Cys Phe Glu Arg Ser Asn Glu Tyr Gln Leu Ile Asp Cys Ala Gln
225                 230                 235                 240 tac ttc ctg gaa aga atc gac agc gtc agc ttg gtt gac tac aca ccc     768
Tyr Phe Leu Glu Arg Ile Asp Ser Val Ser Leu Val Asp Tyr Thr Pro
                245                 250                 255 aca gac cag gac ctc ctc aga tgc aga gtt ctg aca tct ggg att ttt     816
Thr Asp Gln Asp Leu Leu Arg Cys Arg Val Leu Thr Ser Gly Ile Phe
            260                 265                 270 gag aca cga ttc caa gtg gac aaa gta aac ttc cac atg ttt gat gtt     864
Glu Thr Arg Phe Gln Val Asp Lys Val Asn Phe His Met Phe Asp Val
        275                 280                 285 ggt ggc cag agg gat gag agg aga aaa tgg atc cag tgc ttt aac gat     912
Gly Gly Gln Arg Asp Glu Arg Arg Lys Trp Ile Gln Cys Phe Asn Asp
    290                 295                 300
```

```
gtc aca gct atc att tac gtc gca gcc tgc agt agc tac aac atg gtg      960
Val Thr Ala Ile Ile Tyr Val Ala Ala Cys Ser Ser Tyr Asn Met Val
305                 310                 315                 320 att cga gaa gat aac aac acc aac agg ctg aga gag tcc ctg gat ctt     1008
Ile Arg Glu Asp Asn Asn Thr Asn Arg Leu Arg Glu Ser Leu Asp Leu
                325                 330                 335 ttt gaa agc atc tgg aac aac agg tgg tta cgg acc att tct atc atc     1056
Phe Glu Ser Ile Trp Asn Asn Arg Trp Leu Arg Thr Ile Ser Ile Ile
            340                 345                 350 ttg ttc ttg aac aaa caa gat atg ctg gca gaa aaa gtc ttg gca ggg     1104
Leu Phe Leu Asn Lys Gln Asp Met Leu Ala Glu Lys Val Leu Ala Gly
        355                 360                 365 aaa tca aaa att gaa gac tat ttc cca gaa tat gca aat tat act gtt     1152
Lys Ser Lys Ile Glu Asp Tyr Phe Pro Glu Tyr Ala Asn Tyr Thr Val
    370                 375                 380 cct gaa gac gca aca cca gat gca gga gaa gat ccc aaa gtt aca aga     1200
Pro Glu Asp Ala Thr Pro Asp Ala Gly Glu Asp Pro Lys Val Thr Arg
385                 390                 395                 400 gcc aag ttc ttt atc cgg gac ctg ttt ttg agg atc agc acg gcc acc     1248
Ala Lys Phe Phe Ile Arg Asp Leu Phe Leu Arg Ile Ser Thr Ala Thr
                405                 410                 415 ggt gac ggc aaa cat tac tgc tac ccg cac ttc acc tgc gcc gtg gac     1296
Gly Asp Gly Lys His Tyr Cys Tyr Pro His Phe Thr Cys Ala Val Asp
            420                 425                 430 aca gag aac atc cgc agg gtg ttc aac gac tgc cgc gac atc atc cag     1344
Thr Glu Asn Ile Arg Arg Val Phe Asn Asp Cys Arg Asp Ile Ile Gln
        435                 440                 445 cgg atg cac ctc aag cag tat gag ctc ttg tga                         1377
Arg Met His Leu Lys Gln Tyr Glu Leu Leu
    450                 455

<210> SEQ ID NO 3
<211> LENGTH: 44
<212> TYPE: RNA
<213> ORGANISM: artificial sequence
<220> FEATURE:
<223> OTHER INFORMATION: an example of the ribozyme of the present
      invention

<400> SEQUENCE: 3
ucgccuccuu cugaugaggc cgaaaggccg aaaccgccuc gcgc                     44

<210> SEQ ID NO 4
<211> LENGTH: 44
<212> TYPE: RNA
<213> ORGANISM: artificial sequence
<220> FEATURE:
<223> OTHER INFORMATION: an example of the ribozyme of the present
      invention

<400> SEQUENCE: 4
cggccgcccg cugaugaggc cgaaaggccg aaacuggggc cagc                     44

<210> SEQ ID NO 5
<211> LENGTH: 43
<212> TYPE: RNA
<213> ORGANISM: artificial sequence
<220> FEATURE:
<223> OTHER INFORMATION: an example of the ribozyme of the present
      invention

<400> SEQUENCE: 5
cagcggccgc cugaugaggc cgaaaggccg aaacuguagc aca                      43
```

<210> SEQ ID NO 6
<211> LENGTH: 54
<212> TYPE: RNA
<213> ORGANISM: artificial sequence
<220> FEATURE:
<223> OTHER INFORMATION: an example of the ribozyme of the present
      invention

<400> SEQUENCE: 6
ucgccuccuu agaagccuac cagagaaaca cacguugugg uauauuaccu ggua        54

<210> SEQ ID NO 7
<211> LENGTH: 54
<212> TYPE: RNA
<213> ORGANISM: artificial sequence
<220> FEATURE:
<223> OTHER INFORMATION: an example of the ribozyme of the present
      invention

<400> SEQUENCE: 7
cggccgcccg agaaggggac cagagaaaca cacguugugg uauauuaccu ggua        54

<210> SEQ ID NO 8
<211> LENGTH: 55
<212> TYPE: RNA
<213> ORGANISM: artificial sequence
<220> FEATURE:
<223> OTHER INFORMATION: an example of the ribozyme of the present
      invention

<400> SEQUENCE: 8
cagcggccgc aagaaguaga ccagagaaac acacguugug guauauuacc uggua       55

<210> SEQ ID NO 9
<211> LENGTH: 24
<212> TYPE: DNA
<213> ORGANISM: artificial sequence
<220> FEATURE:
<223> OTHER INFORMATION: an example of the oligonucleotide of the
      present invention

<400> SEQUENCE: 9
atgggtctgt gctacagtct gcgg                                         24

<210> SEQ ID NO 10
<211> LENGTH: 37
<212> TYPE: DNA
<213> ORGANISM: artificial sequence
<220> FEATURE:
<223> OTHER INFORMATION: an example of the oligonucleotide of the
      present invention

<400> SEQUENCE: 10
acgatggtgc ttttcccaga ctcaccagcc ccgagca                           37

<210> SEQ ID NO 11
<211> LENGTH: 24
<212> TYPE: DNA
<213> ORGANISM: artificial sequence
<220> FEATURE:
<223> OTHER INFORMATION: a primer used in an example of the present
      invention

<400> SEQUENCE: 11
atgggtctgt gctacagtct gcgg                                         24

```
<210> SEQ ID NO 12
<211> LENGTH: 21
<212> TYPE: DNA
<213> ORGANISM: artificial sequence
<220> FEATURE:
<223> OTHER INFORMATION: a primer used in an example of the present
      invention

<400> SEQUENCE: 12
tcacaagagc tcatactgct t                                              21

<210> SEQ ID NO 13
<211> LENGTH: 22
<212> TYPE: DNA
<213> ORGANISM: artificial sequence
<220> FEATURE:
<223> OTHER INFORMATION: a primer used in an example of the present
      invention

<400> SEQUENCE: 13
atggggtgtt tgggcggcaa ca                                             22

<210> SEQ ID NO 14
<211> LENGTH: 37
<212> TYPE: DNA
<213> ORGANISM: artificial sequence
<220> FEATURE:
<223> OTHER INFORMATION: a primer used in an example of the present
      invention

<400> SEQUENCE: 14
acgatggtgc ttttcccaga ctcaccagcc ccgagca                             37

<210> SEQ ID NO 15
<211> LENGTH: 29
<212> TYPE: DNA
<213> ORGANISM: artificial sequence
<220> FEATURE:
<223> OTHER INFORMATION: a primer used in an example of the present
      invention

<400> SEQUENCE: 15
atgggcctat gctacagcct gcggccgct                                      29

<210> SEQ ID NO 16
<211> LENGTH: 36
<212> TYPE: DNA
<213> ORGANISM: artificial sequence
<220> FEATURE:
<223> OTHER INFORMATION: a primer used in an example of the present
      invention

<400> SEQUENCE: 16
gctgcaggtc ccgcttctgc tcgcgcagca tgcggt                              36

<210> SEQ ID NO 17
<211> LENGTH: 36
<212> TYPE: DNA
<213> ORGANISM: artificial sequence
<220> FEATURE:
<223> OTHER INFORMATION: a primer used in an example of the present
      invention

<400> SEQUENCE: 17
agctcggatc catgaggact ctgaacacct ctgcca                              36
```

<210> SEQ ID NO 18
<211> LENGTH: 34
<212> TYPE: DNA
<213> ORGANISM: artificial sequence
<220> FEATURE:
<223> OTHER INFORMATION: a primer used in an example of the present
      invention

<400> SEQUENCE: 18
gtgcagaatt ctcatctgcg agttcaggtt gggt                              34

<210> SEQ ID NO 19
<211> LENGTH: 40
<212> TYPE: DNA
<213> ORGANISM: artificial sequence
<220> FEATURE:
<223> OTHER INFORMATION: a primer used in an example of the present
      invention

<400> SEQUENCE: 19
agctcggatc catggatcca ctgaatctgt cctggtatga                        40

<210> SEQ ID NO 20
<211> LENGTH: 41
<212> TYPE: DNA
<213> ORGANISM: artificial sequence
<220> FEATURE:
<223> OTHER INFORMATION: a primer used in an example of the present
      invention

<400> SEQUENCE: 20
gtgcagaatt ctcagcagtg aaggatcttc tggaaggcct t                      41

<210> SEQ ID NO 21
<211> LENGTH: 26
<212> TYPE: DNA
<213> ORGANISM: artificial sequence
<220> FEATURE:
<223> OTHER INFORMATION: a primer used in an example of the present
      invention

<400> SEQUENCE: 21
atgagtgagc ttgaccagtt acggca                                      26

<210> SEQ ID NO 22
<211> LENGTH: 26
<212> TYPE: DNA
<213> ORGANISM: artificial sequence
<220> FEATURE:
<223> OTHER INFORMATION: a primer used in an example of the present
      invention

<400> SEQUENCE: 22
ttagttccag atcttgagga agctat                                      26

<210> SEQ ID NO 23
<211> LENGTH: 25
<212> TYPE: DNA
<213> ORGANISM: artificial sequence
<220> FEATURE:
<223> OTHER INFORMATION: a primer used in an example of the present
      invention

<400> SEQUENCE: 23
atgaaaggtg agaccccggt gaaca                                       25

<210> SEQ ID NO 24

```
<211> LENGTH: 24
<212> TYPE: DNA
<213> ORGANISM: artificial sequence
<220> FEATURE:
<223> OTHER INFORMATION: a primer used in an example of the present
      invention

<400> SEQUENCE: 24
tcagaggaga gcacagaaga actt                                                24

<210> SEQ ID NO 25
<211> LENGTH: 448
<212> TYPE: PRT
<213> ORGANISM: Mus musculus

<400> SEQUENCE: 25
```

Met Gly Leu Cys Tyr Ser Leu Arg Pro Leu Phe Gly Ser Pro Glu
 1               5                  10                  15

Asp Thr Pro Cys Ala Ala Ser Glu Pro Cys Ala Glu Asp Ala Gln Pro
                20                  25                  30

Ser Ala Ala Pro Ala Pro Ala Ser Ile Pro Ala Pro Ala Pro Val Gly
        35                  40                  45

Thr Leu Leu Arg Arg Gly Gly Arg Ile Val Ala Asn Ala Arg Pro
    50                  55                  60

Pro Gly Glu Leu Gln Ser Arg Arg Gln Gln Leu Arg Ala Glu
65                  70                  75                  80

Glu Arg Glu Ala Ala Lys Glu Ala Arg Lys Val Ser Arg Gly Ile Asp
                85                  90                  95

Arg Met Leu Arg Glu Gln Lys Arg Asp Leu Gln Gln Thr His Arg Leu
            100                 105                 110

Leu Leu Leu Gly Ala Gly Glu Ser Gly Lys Ser Thr Ile Val Lys Gln
        115                 120                 125

Met Arg Ile Leu His Val Asn Gly Phe Asn Pro Glu Glu Lys Lys Gln
    130                 135                 140

Lys Ile Leu Asp Ile Arg Lys Asn Val Lys Asp Ala Ile Val Thr Ile
145                 150                 155                 160

Val Ser Ala Met Ser Thr Ile Ile Pro Pro Val Pro Leu Ala Asn Pro
                165                 170                 175

Glu Asn Gln Phe Arg Ser Asp Tyr Ile Lys Ser Ile Ala Pro Ile Thr
            180                 185                 190

Asp Phe Glu Tyr Ser Gln Glu Phe Phe Asp His Val Lys Lys Leu Trp
        195                 200                 205

Asp Asp Glu Gly Val Lys Ala Cys Phe Glu Arg Ser Asn Glu Tyr Gln
    210                 215                 220

Leu Ile Asp Cys Ala Gln Tyr Phe Leu Glu Arg Ile Asp Ser Val Ser
225                 230                 235                 240

Leu Val Asp Tyr Thr Pro Thr Asp Gln Asp Leu Leu Arg Cys Arg Val
                245                 250                 255

Leu Thr Ser Gly Ile Phe Glu Thr Arg Phe Gln Val Asp Lys Val Asn
            260                 265                 270

Phe His Met Phe Asp Val Gly Gly Gln Arg Asp Glu Arg Arg Lys Trp
        275                 280                 285

Ile Gln Cys Phe Asn Asp Val Thr Ala Ile Ile Tyr Val Ala Ala Cys
    290                 295                 300

Ser Ser Tyr Asn Met Val Ile Arg Glu Asp Asn Asn Thr Asn Arg Leu
305                 310                 315                 320

```
Arg Glu Ser Leu Asp Leu Phe Glu Ser Ile Trp Asn Asn Arg Trp Leu
            325                 330                 335

Arg Thr Ile Ser Ile Ile Leu Phe Leu Asn Lys Gln Asp Met Leu Ala
            340                 345                 350

Glu Lys Val Leu Ala Gly Lys Ser Lys Ile Glu Asp Tyr Phe Pro Glu
            355                 360                 365

Tyr Ala Asn Tyr Thr Val Pro Glu Asp Ala Thr Pro Asp Ala Gly Glu
            370                 375                 380

Asp Pro Lys Val Thr Arg Ala Lys Phe Phe Ile Arg Asp Leu Phe Leu
385                 390                 395                 400

Arg Ile Ser Thr Ala Thr Gly Asp Gly Lys His Tyr Cys Tyr Pro His
                405                 410                 415

Phe Thr Cys Ala Val Asp Thr Glu Asn Ile Arg Arg Val Phe Asn Asp
            420                 425                 430

Cys Arg Asp Ile Ile Gln Arg Met His Leu Lys Gln Tyr Glu Leu Leu
            435                 440                 445

<210> SEQ ID NO 26
<211> LENGTH: 450
<212> TYPE: PRT
<213> ORGANISM: Rattus norvegicus

<400> SEQUENCE: 26

Met Gly Leu Cys Tyr Ser Leu Arg Pro Leu Phe Gly Ser Ser Gly
 1               5                  10                  15

Asp Ala Pro Cys Glu Asp Ser Glu Pro Cys Ala Glu Asp Ala Gln Pro
                20                  25                  30

Ser Ala Ala Pro Ala Pro Ala Pro Ile Pro Ala Pro Ala Pro
            35                  40                  45

Val Gly Thr Leu Leu Arg Arg Gly Asp Gly Arg Ile Pro Ala Ser Ala
        50                  55                  60

Arg Ser Pro Val Glu Leu Gln Asn Arg Arg Gln Glu Gln Leu Arg
 65                 70                  75                  80

Ala Glu Glu Arg Glu Ala Ala Lys Glu Ala Arg Lys Val Ser Arg Gly
                85                  90                  95

Ile Asp Arg Met Leu Arg Glu Gln Lys Arg Asp Leu Gln Gln Thr His
            100                 105                 110

Arg Leu Leu Leu Leu Gly Ala Gly Glu Ser Gly Lys Ser Thr Ile Val
        115                 120                 125

Lys Gln Met Arg Ile Leu His Val Asn Gly Phe Asn Pro Glu Glu Lys
    130                 135                 140

Lys Gln Lys Ile Leu Asp Ile Arg Lys Asn Val Lys Asp Ala Leu Val
145                 150                 155                 160

Thr Ile Ile Ser Ala Met Ser Thr Ile Ile Pro Val Pro Leu Ala
                165                 170                 175

Asn Pro Glu Asn Gln Phe Arg Ser Asp Tyr Ile Lys Ser Ile Ala Pro
            180                 185                 190

Ile Thr Asp Phe Glu Tyr Ser Gln Glu Phe Phe Asp His Val Lys Lys
        195                 200                 205

Leu Trp Asp Asp Glu Gly Val Lys Ala Cys Phe Glu Arg Ser Asn Glu
    210                 215                 220

Tyr Gln Leu Ile Asp Cys Ala Gln Tyr Phe Leu Glu Arg Ile Asp Ser
225                 230                 235                 240

Val Ser Leu Val Asp Tyr Thr Pro Thr Asp Gln Asp Leu Leu Arg Cys
                245                 250                 255
```

-continued

```
Arg Val Leu Thr Ser Gly Ile Phe Glu Thr Arg Phe Gln Val Asp Lys
            260                 265                 270
Val Asn Phe His Met Phe Asp Val Gly Gly Gln Arg Asp Glu Arg Arg
        275                 280                 285
Lys Trp Ile Gln Cys Phe Asn Asp Val Thr Ala Ile Ile Tyr Val Ala
    290                 295                 300
Ala Cys Ser Ser Tyr Asn Met Val Ile Arg Glu Asp Asn Asn Thr Asn
305                 310                 315                 320
Arg Leu Arg Glu Ser Leu Asp Leu Phe Glu Ser Ile Trp Asn Asn Arg
            325                 330                 335
Trp Leu Arg Thr Ile Ser Ile Ile Leu Phe Leu Asn Lys Gln Asp Met
        340                 345                 350
Leu Ala Glu Lys Val Leu Ala Gly Lys Ser Lys Ile Glu Asp Tyr Phe
    355                 360                 365
Pro Glu Tyr Ala Asn Tyr Thr Val Pro Glu Asp Ala Thr Pro Asp Ala
370                 375                 380
Gly Glu Asp Pro Lys Val Thr Arg Ala Lys Phe Phe Ile Arg Asp Leu
385                 390                 395                 400
Phe Leu Arg Ile Ser Thr Ala Thr Gly Asp Gly Lys His Tyr Cys Tyr
            405                 410                 415
Pro His Phe Thr Cys Ala Val Asp Thr Glu Asn Ile Arg Arg Val Phe
        420                 425                 430
Asn Asp Cys Arg Asp Ile Ile Gln Arg Met His Leu Lys Gln Tyr Glu
    435                 440                 445
Leu Leu
    450

<210> SEQ ID NO 27
<211> LENGTH: 1347
<212> TYPE: DNA
<213> ORGANISM: Mus musculus
<220> FEATURE:
<221> NAME/KEY: CDS
<222> LOCATION: (1)..(1347)

<400> SEQUENCE: 27 atg ggc cta tgc tac agc ctg cgg ccg ctg ctc ttc ggg agc cca gag      48
Met Gly Leu Cys Tyr Ser Leu Arg Pro Leu Leu Phe Gly Ser Pro Glu
 1               5                  10                  15 gac acc ccg tgt gcg gcc tcg gaa ccc tgc gca gag gat gct cag ccc      96
Asp Thr Pro Cys Ala Ala Ser Glu Pro Cys Ala Glu Asp Ala Gln Pro
                20                  25                  30 agc gcc gcc ccg gcc cct gcc tcg atc cca gcc ccg gct ccc gta ggg     144
Ser Ala Ala Pro Ala Pro Ala Ser Ile Pro Ala Pro Ala Pro Val Gly
            35                  40                  45 acc ctg ctc cgg cgt ggc ggc ggc cgg atc gtc gcg aac gcg cgg ccg     192
Thr Leu Leu Arg Arg Gly Gly Gly Arg Ile Val Ala Asn Ala Arg Pro
        50                  55                  60 cca ggc gag ctg cag agc cgc cgg cga cag gag cag cta cga gcc gag     240
Pro Gly Glu Leu Gln Ser Arg Arg Arg Gln Glu Gln Leu Arg Ala Glu
 65                  70                  75                  80 gag cgc gag gcg gct aaa gag gcg agg aaa gtc agc cgg ggc atc gac     288
Glu Arg Glu Ala Ala Lys Glu Ala Arg Lys Val Ser Arg Gly Ile Asp
                85                  90                  95 cgc atg ctg cgc gag cag aag cgg gac ctg cag cag acg cac cgg ctc     336
Arg Met Leu Arg Glu Gln Lys Arg Asp Leu Gln Gln Thr His Arg Leu
                100                 105                 110
```

```
ctg ctg ctg ggg gct ggt gag tcc ggg aaa agc act atc gtc aaa cag      384
Leu Leu Leu Gly Ala Gly Glu Ser Gly Lys Ser Thr Ile Val Lys Gln
        115                 120                 125 atg agg atc ctg cac gtc aat ggc ttc aac ccc gag gaa aag aag cag      432
Met Arg Ile Leu His Val Asn Gly Phe Asn Pro Glu Glu Lys Lys Gln
130                 135                 140 aaa att ctg gac atc agg aaa aat gtc aaa gat gcg atc gtg aca atc      480
Lys Ile Leu Asp Ile Arg Lys Asn Val Lys Asp Ala Ile Val Thr Ile
145                 150                 155                 160 gtt tca gca atg agt act atc ata cct cca gtt cca ctg gcc aac cct      528
Val Ser Ala Met Ser Thr Ile Ile Pro Pro Val Pro Leu Ala Asn Pro
                165                 170                 175 gag aac cag ttc cgg tca gat tat atc aag agc ata gcc cct atc act      576
Glu Asn Gln Phe Arg Ser Asp Tyr Ile Lys Ser Ile Ala Pro Ile Thr
            180                 185                 190 gac ttt gaa tat tcc cag gag ttc ttt gac cat gtg aag aag ctg tgg      624
Asp Phe Glu Tyr Ser Gln Glu Phe Phe Asp His Val Lys Lys Leu Trp
        195                 200                 205 gac gat gaa gga gtg aag gcc tgc ttt gag aga tcc aac gag tac cag      672
Asp Asp Glu Gly Val Lys Ala Cys Phe Glu Arg Ser Asn Glu Tyr Gln
210                 215                 220 ctg atc gac tgt gca caa tac ttc ctg gaa agg att gac agt gtc agt      720
Leu Ile Asp Cys Ala Gln Tyr Phe Leu Glu Arg Ile Asp Ser Val Ser
225                 230                 235                 240 ctg gtt gac tac aca ccc aca gac cag gac ctg ctc aga tgc aga gtg      768
Leu Val Asp Tyr Thr Pro Thr Asp Gln Asp Leu Leu Arg Cys Arg Val
                245                 250                 255 ctg aca tca gga atc ttt gag aca cga ttc caa gtg gac aaa gtg aac      816
Leu Thr Ser Gly Ile Phe Glu Thr Arg Phe Gln Val Asp Lys Val Asn
            260                 265                 270 ttt cac atg ttt gat gtt gga ggc cag aga gat gag aga aga aaa tgg      864
Phe His Met Phe Asp Val Gly Gly Gln Arg Asp Glu Arg Arg Lys Trp
        275                 280                 285 atc cag tgt ttt aat gat gtc act gcg atc att tac gtg gcg gcc tgt      912
Ile Gln Cys Phe Asn Asp Val Thr Ala Ile Ile Tyr Val Ala Ala Cys
290                 295                 300 agc agc tac aac atg gtg atc cgg gaa gat aac aat acc aac aga ctt      960
Ser Ser Tyr Asn Met Val Ile Arg Glu Asp Asn Asn Thr Asn Arg Leu
305                 310                 315                 320 cgg gaa tca ctg gac ctg ttt gaa agc atc tgg aat aac agg tgg ttg     1008
Arg Glu Ser Leu Asp Leu Phe Glu Ser Ile Trp Asn Asn Arg Trp Leu
                325                 330                 335 cga acc att tct atc atc cta ttc ttg aac aaa caa gac atg ctg gca     1056
Arg Thr Ile Ser Ile Ile Leu Phe Leu Asn Lys Gln Asp Met Leu Ala
            340                 345                 350 gaa aaa gtc ttg gca ggg aag tca aaa atc gaa gac tat ttc ccg gag     1104
Glu Lys Val Leu Ala Gly Lys Ser Lys Ile Glu Asp Tyr Phe Pro Glu
        355                 360                 365 tat gcc aat tat act gtc cct gaa gat gca aca cca gat gcg gga gaa     1152
Tyr Ala Asn Tyr Thr Val Pro Glu Asp Ala Thr Pro Asp Ala Gly Glu
370                 375                 380 gat ccc aaa gtt aca aga gca aag ttc ttt atc cgg gat ctg ttc ttg     1200
Asp Pro Lys Val Thr Arg Ala Lys Phe Phe Ile Arg Asp Leu Phe Leu
385                 390                 395                 400 agg atc agc aca gcc acg ggt gat ggc aaa cat tac tgc tac cct cac     1248
Arg Ile Ser Thr Ala Thr Gly Asp Gly Lys His Tyr Cys Tyr Pro His
                405                 410                 415 ttc acc tgc gcc gtg gac aca gag aac atc cgc aga gtg ttc aac gat     1296
Phe Thr Cys Ala Val Asp Thr Glu Asn Ile Arg Arg Val Phe Asn Asp
            420                 425                 430
```

```
tgc cgt gac atc atc cag aga atg cat ctc aag cag tac gaa ctc ttg      1344
Cys Arg Asp Ile Ile Gln Arg Met His Leu Lys Gln Tyr Glu Leu Leu
        435                 440                 445 tga                                                                   1347

<210> SEQ ID NO 28
<211> LENGTH: 1353
<212> TYPE: DNA
<213> ORGANISM: Rattus norvegicus
<220> FEATURE:
<221> NAME/KEY: CDS
<222> LOCATION: (1)..(1353)

<400> SEQUENCE: 28 atg ggc ctg tgc tac agc cta cgg ccg ctg ctc ttc ggg agc tcg ggg        48
Met Gly Leu Cys Tyr Ser Leu Arg Pro Leu Leu Phe Gly Ser Ser Gly
  1               5                  10                  15 gac gcc ccc tgt gag gac tct gag ccg tgc gct gag gat gct cag ccc        96
Asp Ala Pro Cys Glu Asp Ser Glu Pro Cys Ala Glu Asp Ala Gln Pro
                 20                  25                  30 agc gcc gcc ccg gcc ccg gcc ccg gcc ccg atc cca gcc ccg gct ccg       144
Ser Ala Ala Pro Ala Pro Ala Pro Ala Pro Ile Pro Ala Pro Ala Pro
             35                  40                  45 gtg ggg acc ctg ctc cgg cga ggc gac ggc cgg atc ccc gca agc gcg       192
Val Gly Thr Leu Leu Arg Arg Gly Asp Gly Arg Ile Pro Ala Ser Ala
         50                  55                  60 agg tcg cca gtc gag ctg cag aac cgc cgg cga cag gag cag ctg cga       240
Arg Ser Pro Val Glu Leu Gln Asn Arg Arg Arg Gln Glu Gln Leu Arg
 65                  70                  75                  80 gcc gag gag cgc gag gca gct aag gag gcg agg aaa gta agc cgg ggt       288
Ala Glu Glu Arg Glu Ala Ala Lys Glu Ala Arg Lys Val Ser Arg Gly
                 85                  90                  95 atc gac cgc atg ctg cgc gaa cag aag cgc gac ctg cag cag acg cac       336
Ile Asp Arg Met Leu Arg Glu Gln Lys Arg Asp Leu Gln Gln Thr His
                100                 105                 110 cgg ctc ctg ctc ttg ggg gct ggt gag tcc ggg aaa agc act ata gtc       384
Arg Leu Leu Leu Leu Gly Ala Gly Glu Ser Gly Lys Ser Thr Ile Val
            115                 120                 125 aaa cag atg agg atc cta cac gtc aat ggc ttc aac ccc gag gaa aag       432
Lys Gln Met Arg Ile Leu His Val Asn Gly Phe Asn Pro Glu Glu Lys
        130                 135                 140 aag caa aaa att ctg gac atc agg aaa aat gtc aag gat gct tta gtg       480
Lys Gln Lys Ile Leu Asp Ile Arg Lys Asn Val Lys Asp Ala Leu Val
145                 150                 155                 160 aca atc att tca gca atg agt acc ata ata cct cca gtt cca ctg gcc       528
Thr Ile Ile Ser Ala Met Ser Thr Ile Ile Pro Pro Val Pro Leu Ala
                165                 170                 175 aac cct gag aac cag ttt cgg tca gat tac atc aag agc ata gcc cct       576
Asn Pro Glu Asn Gln Phe Arg Ser Asp Tyr Ile Lys Ser Ile Ala Pro
            180                 185                 190 atc act gac ttt gaa tat tcc cag gag ttc ttt gac cac gtg aag aag       624
Ile Thr Asp Phe Glu Tyr Ser Gln Glu Phe Phe Asp His Val Lys Lys
        195                 200                 205 ctg tgg gat gat gag gga gtg aag gcc tgc ttt gag aga tcc aac gag       672
Leu Trp Asp Asp Glu Gly Val Lys Ala Cys Phe Glu Arg Ser Asn Glu
    210                 215                 220 tac cag ctg atc gac tgt gca caa tac ttc ctg gaa agg att gac agc       720
Tyr Gln Leu Ile Asp Cys Ala Gln Tyr Phe Leu Glu Arg Ile Asp Ser
225                 230                 235                 240 gtg agt ctg gtt gac tac aca ccc aca gac cag gac cta ctc aga tgc       768
Val Ser Leu Val Asp Tyr Thr Pro Thr Asp Gln Asp Leu Leu Arg Cys
```

```
                        245                 250                 255
aga gtg ctg aca tca ggg atc ttt gag aca cga ttc caa gtg gac aaa        816
Arg Val Leu Thr Ser Gly Ile Phe Glu Thr Arg Phe Gln Val Asp Lys
            260                 265                 270 gtg aac ttt cac atg ttt gac gtt gga ggc cag agg gat gag aga aga        864
Val Asn Phe His Met Phe Asp Val Gly Gly Gln Arg Asp Glu Arg Arg
        275                 280                 285 aaa tgg atc cag tgt ttt aac gat gtc act gcc atc atc tat gtg gca        912
Lys Trp Ile Gln Cys Phe Asn Asp Val Thr Ala Ile Ile Tyr Val Ala
    290                 295                 300 gcc tgc agc agc tac aac atg gtg atc cgg gaa gat aac aac acc aac        960
Ala Cys Ser Ser Tyr Asn Met Val Ile Arg Glu Asp Asn Asn Thr Asn
305                 310                 315                 320 aga ctc cgg gag tcg ctg gac ctg ttt gaa agc atc tgg aat aac agg       1008
Arg Leu Arg Glu Ser Leu Asp Leu Phe Glu Ser Ile Trp Asn Asn Arg
                325                 330                 335 tgg tta cga acc att tcc atc atc ctg ttc ttg aac aaa caa gat atg       1056
Trp Leu Arg Thr Ile Ser Ile Ile Leu Phe Leu Asn Lys Gln Asp Met
            340                 345                 350 ctg gca gaa aaa gtc ttg gcc ggg aag tca aaa att gaa gac tat ttc       1104
Leu Ala Glu Lys Val Leu Ala Gly Lys Ser Lys Ile Glu Asp Tyr Phe
        355                 360                 365 ccg gag tat gcc aac tat act gtc cct gaa gat gca aca cca gat gca       1152
Pro Glu Tyr Ala Asn Tyr Thr Val Pro Glu Asp Ala Thr Pro Asp Ala
    370                 375                 380 gga gaa gat ccc aaa gtt aca aga gcc aag ttc ttt atc cgg gat ctg       1200
Gly Glu Asp Pro Lys Val Thr Arg Ala Lys Phe Phe Ile Arg Asp Leu
385                 390                 395                 400 ttc ttg agg atc agc aca gcc acg ggt gat ggc aaa cat tac tgc tac       1248
Phe Leu Arg Ile Ser Thr Ala Thr Gly Asp Gly Lys His Tyr Cys Tyr
                405                 410                 415 cct cac ttc acc tgc gcc gtg gac aca gag aac atc cgc aga gtg ttc       1296
Pro His Phe Thr Cys Ala Val Asp Thr Glu Asn Ile Arg Arg Val Phe
            420                 425                 430 aac gat tgt cgt gac atc atc cag aga atg cac ctc aag cag tac gaa       1344
Asn Asp Cys Arg Asp Ile Ile Gln Arg Met His Leu Lys Gln Tyr Glu
        435                 440                 445 ctc ttg tga                                                           1353
Leu Leu
    450

<210> SEQ ID NO 29
<211> LENGTH: 29
<212> TYPE: DNA
<213> ORGANISM: Artificial Sequence
<220> FEATURE:
<223> OTHER INFORMATION: a primer used in an example of the present
      invention

<400> SEQUENCE: 29
atgggcctat gctacagcct gcggccgct                                        29

<210> SEQ ID NO 30
<211> LENGTH: 33
<212> TYPE: DNA
<213> ORGANISM: Artificial Sequence
<220> FEATURE:
<223> OTHER INFORMATION: a primer used in an example of the present
      invention

<400> SEQUENCE: 30
tcacaagagt tcgtactgct tgagatgcat tct                                   33
```

```
<210> SEQ ID NO 31
<211> LENGTH: 30
<212> TYPE: DNA
<213> ORGANISM: Artificial Sequence
<220> FEATURE:
<223> OTHER INFORMATION: a primer used in an example of the present
      invention

<400> SEQUENCE: 31
atgggcctgt gctacagcct acggccgctg                                          30

<210> SEQ ID NO 32
<211> LENGTH: 33
<212> TYPE: DNA
<213> ORGANISM: Artificial Sequence
<220> FEATURE:
<223> OTHER INFORMATION: a primer used in an example of the present
      invention

<400> SEQUENCE: 32
tcacaagagt tcgtactgct tgaggtgcat tct                                      33

<210> SEQ ID NO 33
<211> LENGTH: 37
<212> TYPE: DNA
<213> ORGANISM: Artificial Sequence
<220> FEATURE:
<223> OTHER INFORMATION: a primer used in an example of the present
      invention

<400> SEQUENCE: 33
agctcggatc catgcccatc atgggctcct cggtgta                                  37

<210> SEQ ID NO 34
<211> LENGTH: 34
<212> TYPE: DNA
<213> ORGANISM: Artificial Sequence
<220> FEATURE:
<223> OTHER INFORMATION: a primer used in an example of the present
      invention

<400> SEQUENCE: 34
gtgcagaatt ctcaggacac tcctgctcca tcct                                     34
```

G PROTEINS, POLYNUCLEOTIDE ENCODING THE SAME AND UTILIZATION THEREOF

BACKGROUND OF THE INVENTION

1. Field of the Invention

The present invention relates to a novel G protein having an ability of amplifying a signal transduction generated by a receptor upon binding to a natural ligand such as amine, peptide, hormone, autacoid, neurotransmitter and the like, as well as a polynucleotide encoding the same. The invention also relates to a method for screening for a substance which regulates the cellular signal transduction mediated by this novel G protein, and the like.

2. Description of the Background Art

A G protein is an important mediator in a signal transduction. Thus, the G protein serves as a transmitter which transport, into a cell, a stimulation signal received by a G protein-coupled receptor (hereinafter sometimes abbreviated as GPCR) which is a seven transmembrane receptor. A GPCR is expressed in a wide variety of tissues, and this signal transduction system was proven to be involved in regulation of a wide variety of cellular functions such as hormone reception, neurotransmission, cell proliferation and differentiation and the like (GENDAI KAGAKU ZOKAN 34, 61 to 70, 1997).

More specifically, a G protein is a heterotrimer formed from α subunit which binds to GTP, β subunit and γ subunit. When a GPCR on a cell membrane surface binds to a ligand such as a hormone or neurotransmitter, the GPCR is activated and its signal is transmitted to a G protein. In the G protein to which the signal has been transmitted, a GDP is released from the inactive form in which a GDP was bound once to the α subunit, and a GTP is then bound instead, whereby converting into an active form.

The active G protein is released from the GPCR while dissociating into a GTP-binding α subunit and βγ subunits. The active G protein promotes or inhibits its target effector such as adenylate cyclase, $Ca^{2+}$ channel, $K^+$ channel, phospholipase Cβ and the like, whereby regulating a variety of the cellular functions. A mammalian G protein α subunit may for example be Gi, Go, Gq, Gt and the like. Typically, a G protein α subunit is classified into any of 4 types, namely, the type which promotes the activity of an adenylate cyclase, the type which inhibits the activity of an adenylate cyclase, the type which promotes the activity of a phospholipase and the type which transmits a signal to a Rho.

A GTP which has been bound to an α subunit of an active G protein is converted into a GDP by the GTPase effect possessed by the α subunit, resulting in the recovery of an inactive form ("Signal Dentatsu", p. 17-30, Nov. 1, 2001, KYORITSU SHUPPANSHA).

GPCR genes and its gene products and GPCR signal transduction pathway-related genes and its gene products are potential causes for diseases (Spiegel et al., J. Clin. Invest. 92: 1119-1125 (1993); MuKusick et al., J. Med. Genet. 30: 1-26 (1993); Lania et al., European J. Endocrinology 145: 543-559(2001)). For example, a certain defect in a V2 vasopressin receptor gene as a GPCR has been proven to induce various forms of a nephrogenic diabetes insipidus (Holtzman et al., Hum. Mol. Genet. 2:1201-1204 (1993)). In addition, variation in Gα subunits are observed in a tumor of growth hormone secreting cells in a pituitary gland which secrets a growth hormone, hyperthyroid tumor, ovarian and renal tumors (Meij, JTA (1996), Mol. Cell. Biochem. 157: 31-38; Aussel, C. et al., (1988), J. Immunol. 140: 215-220). Accordingly, GPCR signal-related gene products are useful as a target of a novel drug, and 50% of currently marketed pharmaceuticals were reported to direct the GPCR as a target (Nature Review Drug Discovery, 1, 7 (2002)).

Generally in screening natural ligands of GPCR, it is important to know which G proteins are to be coupled with the GPCR (Trends in Pharmacological Science, 22, 560-564 (2001)). Accordingly, identification of a novel G protein and a gene encoding the same is useful in treating or diagnosing a disease caused by the abnormality in the cellular signal transduction in which said G protein is involved. In addition, it can be used in the screening for a pharmaceutical which is useful as a remedial, therapeutic or prophylactic agent against a disease caused by the abnormality in a cellular signal transduction. Furthermore, it can be used in the screening for a pharmaceutical which is useful as a remedial, therapeutic or prophylactic agent capable of ameliorating or preventing a symptom by means of the activation or inhibition of the cellular signal transduction.

SUMMARY OF THE INVENTION

A main object of the present invention is to provide a novel G protein α subunit and a polynucleotide encoding the same, a substance capable of activating or inhibiting the signal transduction system mediated by a G protein-coupled receptor and this G protein α subunit, a method for screening for such a substance as well as a screening kit therefor.

For the purpose of accomplishing the objective described above, we made an effort and finally discovered a human novel protein comprising an amino acid sequence having a high homology with the GTP binding site and the GTPase activation site conserved among G protein α subunits and an amino acid sequence having a high homology with the heterotrimer forming domain conserved among the G protein α subunits, and designated this protein as a Gm1 protein. We also discovered a mouse Gm1 protein and a rat Gm1 protein having similar characteristics with regard to the amino acid sequences.

Moreover, we discovered that in a cell having a Gm1 expression vector, the effector activity of the G protein is elevated.

Furthermore, we discovered that Gm1 protein is expressed at a high level in human brain, thymus, testes, spleen, small intestine, uterus and heart.

Based on the findings described above, we believed that the present protein (Gm1 protein) is a novel G protein α subunit which is a molecule involved in the signal transduction mediated by a GPCR stimulation which functions in human brain, thymus, testes, spleen, small intestine, uterus and heart, thus establishing the present invention.

Thus, the invention provides the proteins and polynucleotides and the like, which are listed in the following respective paragraphs:

1. A protein comprising any amino acid sequence selected from the group consisting of:
   (a) the amino acid sequence represented by SEQ ID No:1;
   (b) an amino acid sequence of a protein involved in a G protein-coupled receptor mediated signal transduction, said protein consists of an amino acid sequence having a homology of 85% or more with the amino acid sequence represented by SEQ ID No:1;
   (c) the amino acid sequence represented by SEQ ID No:25;
   (d) the amino acid sequence represented by SEQ ID No:26;
   (e) an amino acid sequence of a protein involved in a G protein-coupled receptor mediated signal transduction, said protein comprises the amino acid sequence of the amino acid Nos. 96 to 126 of SEQ ID No:1;

(f) an amino acid sequence of a protein involved in a G protein-coupled receptor mediated signal transduction, said protein comprises an amino acid sequence having a homology of 95% or more with the amino acid sequence of the amino acid Nos. 96 to 126 of SEQ ID No:1;

(g) an amino acid sequence of a protein involved in a G protein-coupled receptor mediated signal transduction, said protein comprises at its N-terminal the amino acid sequence of the amino acid Nos. 1 to 126 of SEQ ID No:1; and (h) an amino acid sequence of a protein involved in a G protein-coupled receptor mediated signal transduction, said protein comprises at its N-terminal an amino acid sequence having a homology of 65% or more with the amino acid sequence of the amino acid Nos. 1 to 126 of SEQ ID No:1.

2. A protein (1) or (2):
(1) the protein consisting of the amino acid sequence represented by SEQ ID No:1;
(2) a protein involved in a G protein-coupled receptor mediated signal transduction which consists of an amino, acid sequence having a homology of 85% or more with the amino acid sequence represented by SEQ ID No:1.

3. The protein consisting of the amino acid sequence represented by SEQ ID No:25.

4. The protein consisting of the amino acid sequence represented by SEQ ID No:26.

5. A protein (3) or (4):
(3) a protein involved in a G protein-coupled receptor mediated signal transduction which comprises the amino acid sequence of the amino acid Nos. 96 to 126 of SEQ ID No:1;
(4) a protein involved in a G protein-coupled receptor mediated signal transduction which comprises an amino acid sequence having a homology of 95% or more with the amino acid sequence of the amino acid Nos. 96 to 126 of SEQ ID No:1.

6. A protein (5) or (6):
(5) a protein involved in a G protein-coupled receptor mediated signal transduction which comprises at its N-terminal the amino acid sequence of the amino acid Nos. 1 to 126 of SEQ ID No:1;
(6) a protein involved in a G protein-coupled receptor mediated signal transduction which comprises at its N-terminal an amino acid sequence having a homology of 65% or more with the amino acid sequence of the amino acid Nos. 1 to 126 of SEQ ID No:1.

7. A polynucleotide comprising a nucleotide sequence selected from the group consisting of:
(a) a nucleotide sequence encoding the amino acid sequence represented by SEQ ID No:1;
(b) a nucleotide sequence encoding an amino acid sequence of a protein involved in a G protein-coupled receptor mediated signal transduction, said protein consists of an amino acid sequence having a homology of 85% or more with the amino acid sequence represented by SEQ ID No:1;
(c) a nucleotide sequence encoding the amino acid sequence represented by SEQ ID No:25;
(d) a nucleotide sequence encoding the amino acid sequence represented by SEQ ID No:26;
(e) a nucleotide sequence encoding an amino acid sequence of a protein involved in a G protein-coupled receptor mediated signal transduction, said protein comprises the amino acid sequence of the amino acid Nos. 96 to 126 of SEQ ID No:1;

(f) a nucleotide sequence encoding an amino acid sequence of a protein involved in a G protein-coupled receptor mediated signal transduction, said protein comprises an amino acid sequence having a homology of 95% or more with the amino acid sequence of the amino acid Nos. 96 to 126 of SEQ ID No:1;

(g) a nucleotide sequence encoding an amino acid sequence of a protein involved in a G protein-coupled receptor mediated signal transduction, said protein comprises at its N-terminal the amino acid sequence of the amino acid Nos. 1 to 126 of SEQ ID No:1;

(h) a nucleotide sequence encoding an amino acid sequence of a protein involved in a G protein-coupled receptor mediated signal transduction, said protein comprises at its N-terminal an amino acid sequence having a homology of 65% or more with the amino acid sequence of the amino acid Nos. 1 to 126 of SEQ ID No:1;

(i) the nucleotide sequence represented by SEQ ID No:2;

(j) a nucleotide sequence of a polynucleotide encoding a protein involved in a G protein-coupled receptor mediated signal transduction, said polynucleotide consists of a nucleotide sequence having a homology of 85% or more with the polynucleotide consisting of the nucleotide sequence represented by SEQ ID No:2;

(k) the nucleotide sequence represented by SEQ ID No:27;

(l) the nucleotide sequence represented by SEQ ID No:28;

(m) a nucleotide sequence of a polynucleotide encoding a protein involved in a G protein-coupled receptor mediated signal transduction, said polynucleotide comprises the nucleotide sequence of the nucleotide Nos. 289 to 378 of SEQ ID No:2;

(n) a nucleotide sequence of a polynucleotide encoding a protein involved in a G protein-coupled receptor mediated signal transduction, said polynucleotide comprises a nucleotide sequence having a homology of 90% or more with the polynucleotide consisting of the nucleotide sequence of the nucleotide Nos. 289 to 378 of SEQ ID No:2;

(o) a nucleotide sequence of a polynucleotide encoding a protein involved in a G protein-coupled receptor mediated signal transduction, said polynucleotide comprises at its 5' terminal the nucleotide sequence of the nucleotide Nos. 1 to 378 of SEQ ID No:2; and (p) a nucleotide sequence of a polynucleotide encoding a protein involved in a G protein-coupled receptor mediated signal transduction, said polynucleotide comprises at its 5' terminal a nucleotide sequence having a homology of 70% or more with the polynucleotide consisting of the nucleotide sequence of the nucleotide Nos. 1 to 378 of SEQ ID No:2.

8. A polynucleotide of (7) or (8):
(7) the polynucleotide consisting of the nucleotide sequence represented by SEQ ID No:2;
(8) a polynucleotide encoding a protein involved in a G protein-coupled receptor mediated signal transduction, said polynucleotide consists of a nucleotide sequence having a homology of 85% or more with the polynucleotide consisting of the nucleotide sequence represented by SEQ ID No:2.

9. The polynucleotide consisting of the nucleotide sequence represented by SEQ ID No:27.

10. The polynucleotide consisting of the nucleotide sequence represented by SEQ ID No:28.

11. A polynucleotide of (9) or (10):
(9) a polynucleotide encoding a protein involved in a G protein-coupled receptor mediated signal transduction, said polynucleotide comprises the nucleotide sequence of the nucleotide Nos. 289 to 378 of SEQ ID No:2;
(10) a polynucleotide encoding a protein involved in a G protein-coupled receptor mediated signal transduction, said polynucleotide comprises a nucleotide sequence having a homology of 90% or more with the polynucleotide consisting of the nucleotide sequence of the nucleotide Nos. 289 to 378 of SEQ ID No:2.

12. A polynucleotide of (11) or (12):
(11) a polynucleotide encoding a protein involved in a G protein-coupled receptor mediated signal transduction, said polynucleotide comprises at its 5' terminal the nucleotide sequence of the nucleotide Nos. 1 to 378 of SEQ ID No:2;
(12) a polynucleotide encoding a protein involved in a G protein-coupled receptor mediated signal transduction, said polynucleotide comprises at its 5' terminal a nucleotide sequence having a homology of 70% or more with the polynucleotide consisting of the nucleotide sequence of the nucleotide Nos. 1 to 378 of SEQ ID No:2.

13. A recombinant vector containing a polynucleotide according to the above 7.

14. A method for producing a recombinant vector comprising a step for integrating a polynucleotide according to the above 7 into a vector capable of being replicated in a host cell.

15. A transformant having a recombinant vector according to the above 13.

16. A method for producing a transformant comprising a step for transducing a recombinant vector according to the above 13 into a host cell.

17. A method for producing a G protein α-subunit comprising steps for culturing a transformant having a recombinant vector containing a polynucleotide according to the above 7 and recovering from the culture a protein resulting from the polynucleotide according to the above 7.

18. An antisense polynucleotide consisting of a polynucleotide of (13) or (14):
(13) a polynucleotide which inhibits the expression of a protein according to the above 1 which comprises a nucleotide sequence complementary to at least 15 contiguous nucleotides in the nucleotide sequence represented by SEQ ID No:2;
(14) a polynucleotide which inhibits the expression of a protein according to the above 1 which hybridizes under an intracellular condition with a polynucleotide consisting of at least 15 contiguous nucleotides in the nucleotide sequence represented by SEQ ID No:2.

19. A ribozyme (15) or (16):
(15) a ribozyme having an ability of cleaving a polynucleotide according to the above 7 which comprises two polynucleotide regions complementary to two regions respectively consisting of at least 9 contiguous nucleotides which are two regions in the nucleotide sequence represented by SEQ ID No:2;
(16) a ribozyme having an ability of cleaving a polynucleotide according to the above 7 which comprises two polynucleotide regions which hybridizes under an intracellular condition with two regions respectively consisting of at least 9 contiguous nucleotides which are two regions in the nucleotide sequence represented by SEQ ID No:2.

20. An antibody which recognizes a protein according to the above 1 specifically.

21. An agent for regulating a G protein-coupled receptor mediated signal transduction containing as an active ingredient a protein according to the above 1.

22. A therapeutic or prophylactic agent against a disease caused by a G protein-coupled receptor mediated signal transduction abnormality, wherein an active ingredient of the agent is a protein according to the above 1.

23. An agent for regulating a G protein-coupled receptor mediated signal transduction containing as an active ingredient a polynucleotide according to the above 7.

24. A therapeutic or prophylactic agent against a disease caused by a G protein-coupled receptor mediated signal transduction abnormality, wherein an active ingredient of the agent is a polynucleotide according to the above 7.

25. An agent for regulating a G protein-coupled receptor mediated signal transduction containing as an active ingredient an antisense polynucleotide according to the above 18.

26. A therapeutic or prophylactic agent against a disease caused by a G protein-coupled receptor mediated signal transduction abnormality, wherein an active ingredient of the agent is an antisense polynucleotide according to the above 18.

27. An agent for regulating a G protein-coupled receptor mediated signal transduction containing as an active ingredient a ribozyme according to the above 19.

28. A therapeutic or prophylactic agent against a disease caused by a G protein-coupled receptor mediated signal transduction abnormality, wherein an active ingredient of the agent is a ribozyme according to the above 19.

29. An agent for regulating a G protein-coupled receptor mediated signal transduction containing as an active ingredient an antibody according to the above 20.

30. A therapeutic or prophylactic agent against a disease caused by a G protein-coupled receptor mediated signal transduction abnormality, wherein an active ingredient of the agent is an antibody according to the above 20.

31. An oligonucleotide (17) or (18):
(17) an oligonucleotide capable of recognizing a polynucleotide represented by SEQ ID NO:2 specifically which consists of at least 17 contiguous nucleotides in the nucleotide sequence represented by SEQ ID No:2;
(18) an oligonucleotide capable of recognizing a polynucleotide represented by SEQ ID NO:2 specifically which has a homology of 80% or more with at least 17 contiguous nucleotides in the nucleotide sequence represented by SEQ ID No;2.

32. An oligonucleotide according to the above 31 which is used as a probe or a primer.

33. A method for screening for a substance capable of regulating a signal transduction mediated by a G protein-coupled receptor and a G protein comprising:
(a) a step for bringing a test substance into contact with a test cell having a recombinant vector according to the above 13 and a recombinant vector containing a DNA encoding a G protein-coupled receptor protein;
(b) a step for measuring the G protein effector activity or the index value correlating therewith in the test cell; and
(c) a step for comparing this effector activity or the index value correlating therewith with the effector activity or the index value correlating therewith in the test cell which has not been brought into contact with the test substance, whereby selecting a test substance capable of altering the effector activity or the index value correlating therewith in the test cell.

34. A method for screening for a substance capable of regulating a signal transduction mediated by a G protein-coupled receptor and a G protein comprising:

(a) a step for bringing a test substance into contact with a test cell having a recombinant vector according to the above 13 and a recombinant vector containing a DNA encoding a G protein-coupled receptor protein;
(b) a step for measuring the G protein effector activity or the index value correlating therewith in the test cell; and
(c) a step for comparing this effector activity with the effector activity or the index value correlating therewith when the said test substance has been brought into contact with a control cell having no recombinant vector according to the above 13 but having a recombinant vector containing a DNA encoding a G protein-coupled receptor protein, whereby selecting a test substance causing a difference in the effector activity or the index value correlating therewith between the test cell and the control cell.

35. A method for screening for a substance capable of regulating a signal transduction mediated by a G protein-coupled receptor and a G protein comprising:
(a) a step for bringing a test substance into contact with a test cell having a recombinant vector according to the above 13 and a recombinant vector containing a DNA encoding a G protein-coupled receptor protein;
(b) a step for measuring the G protein effector activity or the index value correlating therewith in the test cell; and
(c) a step for comparing this effector activity or the index value correlating therewith with the effector activity or the index value correlating therewith when the said test substance has been brought into contact with a control cell having no recombinant vector containing a DNA encoding a G protein-coupled receptor protein but having a recombinant vector according to the above 13, whereby selecting a test substance causing a difference in the effector activity or the index value correlating therewith between the test cell and the control cell.

36. A method for screening for a substance capable of regulating a signal transduction mediated by a G protein-coupled receptor and a G protein comprising:
(a) a step for bringing a test substance and a G protein-coupled receptor ligand into contact with a test cell having a recombinant vector according to the above 13 and a recombinant vector containing a DNA encoding a G protein-coupled receptor protein;
(b) a step for measuring the G protein effector activity or the index value correlating therewith in the test cell; and
(c) a step for comparing this effector activity or the index value correlating therewith with the effector activity or the index value correlating therewith in the test cell which has not been brought into contact with the test substance but has been brought into contact with the ligand, whereby selecting a test substance capable of altering the effector activity or the index value correlating therewith in the test cell.

37. A method for screening for a substance capable of regulating a signal transduction mediated by a G protein-coupled receptor and a G protein comprising:
(a) a step for bringing a test substance and a G protein-coupled receptor ligand into contact with a test cell having a recombinant vector according to the above 13 and a recombinant vector containing a DNA encoding a G protein-coupled receptor protein;
(b) a step for measuring the G protein effector activity or the index value correlating therewith in the test cell;
(c) a step for comparing this effector activity with the effector activity in the test cell which has not been brought into contact with the test substance but has been brought into contact with the ligand, whereby investigating the change in the effector activity in the test cell; and
(d) a step for comparing the rate of change in this effector activity or the index value correlating therewith with the rate of change in the effector activity or the index value correlating therewith when the said test substance and said ligand has been brought into contact with a control cell having no recombinant vector containing a DNA encoding a G protein-coupled receptor protein but having a recombinant vector according to the above 13, whereby selecting a test substance causing a difference in the rate of change in the effector activity or the index value correlating therewith between the test cell and the control cell.

38. A method for screening for a substance capable of regulating a signal transduction mediated by a G protein-coupled receptor and a G protein comprising:
(a) a step for bringing a test substance into contact with a cell membrane fraction of a cell having a recombinant vector according to the above 13 and a cell membrane fraction of a cell having a recombinant vector containing a DNA encoding a GPCR, or
a cell membrane fraction of a cell having the recombinant vector according to the above 13 and the recombinant vector containing the DNA encoding the GPCR;
(b) a step for assaying the level of the binding of GTP to the cell membrane fraction; and
(c) a step for comparing the assayed level of this GTP binding with the assayed level of the GTP binding to the cell membrane fraction which has not been brought into contact with the test substance, whereby selecting a test substance capable of altering the assayed level of the GTP binding to the cell membrane fraction.

39. A method for screening for a substance capable of regulating a signal transduction mediated by a G protein-coupled receptor and a G protein comprising:
(a) a step for bringing a test substance and a G protein-coupled receptor ligand into contact with
a cell membrane fraction of a cell having a recombinant vector according to the above 13 and a cell membrane fraction of a cell having a recombinant vector containing a DNA encoding a GPCR, or
a cell membrane fraction of a cell having the recombinant vector according to the above 13 and the recombinant vector containing the DNA encoding the GPCR;
(b) a step for assaying the level of the binding of GTP to the cell membrane fraction; and
(c) a step for comparing the assayed level of this GTP binding with the assayed level of the GTP binding in the cell membrane fraction which has not been brought into contact with the test substance but has been brought into contact with said ligand, whereby selecting a test substance capable of altering the assayed level of the GTP binding to the cell membrane fraction.

40. A method for screening for a substance capable of regulating a signal transduction mediated by a G protein-coupled receptor and a G protein comprising:
(a) a step for bringing a test substance into contact with a test cell capable of expressing a protein according to the above 1;
(b) a step for measuring the expression level of the protein according to the above 1 in the test cell; and
(c) a step for comparing this expression level with the expression level of said protein in the test cell which has not been brought into contact with the test substance, whereby selecting a test substance capable of altering the expression level of said protein in the test cell.

41. A substance capable of regulating a signal transduction mediated by a G protein-coupled receptor and a G protein, said substance is obtained by a screening method according to any of the above 33 to 40.

42. An agent for regulating a signal transduction mediated by a G protein-coupled receptor and a G protein, said agent contains as an active ingredient a substance according to the above 41.

43. A therapeutic or prophylactic agent against a disease caused by the abnormality in a G protein-coupled receptor and a G protein-mediated signal transduction containing as an active ingredient a substance according to the above 41.

44. A kit for screening for a substance capable of regulating a signal transduction mediated by a G protein-coupled receptor and a protein according to the above 1, which comprises a test cell having a recombinant vector containing a polynucleotide encoding a protein according to the above 1 and a reagent for measuring the G protein effector activity or an index value correlating therewith.

45. A screening kit according to the above 44 wherein the test cell further has a recombinant vector having a DNA encoding a G protein-coupled receptor.

46. A screening kit according to the above 44 further containing a G protein-coupled receptor ligand.

47. A screening kit according to the above 44 further containing a control cell having a recombinant vector having a DNA encoding a G protein-coupled receptor.

48. A screening kit according to the above 44 further containing a control cell having a recombinant vector containing a polynucleotide encoding a protein according to the above 1.

49. A kit for screening for a substance capable of regulating a signal transduction mediated by a G protein-coupled receptor and a protein according to the above 1, which comprises:
a cell having a recombinant vector containing a polynucleotide encoding a protein according to the above 1; and,
a GTP analogue which can bind to the protein according to the above 1 but can not be cleaved by a GTPase.

50. A screening kit according to the above 49 wherein the cell further has a recombinant vector having a DNA encoding a G protein-coupled receptor.

51. A kit for screening for a substance capable of regulating a signal transduction mediated by a G protein-coupled receptor and a protein according to the above 1, which comprises:
a cell having a recombinant vector containing a polynucleotide encoding a protein according to the above 1;
a cell having a recombinant vector having a DNA encoding the G protein-coupled receptor; and,
a GTP analogue which can bind to the protein according to the above 1 but can not be cleaved by a GTPase.

52. A screening kit according to the above 49 or 51 further containing a G protein-coupled receptor ligand.

53. A kit for screening for a substance capable of regulating a signal transduction mediated by a G protein-coupled receptor and a protein according to the above 1, which comprises:
a cell capable of expressing a protein according to the above 1; and
an oligonucleotide according to the above 31 or an antibody according to the above 20.

DESCRIPTION OF THE PREFERRED EMBODIMENTS

<Inventive Proteins>

Figure 1:
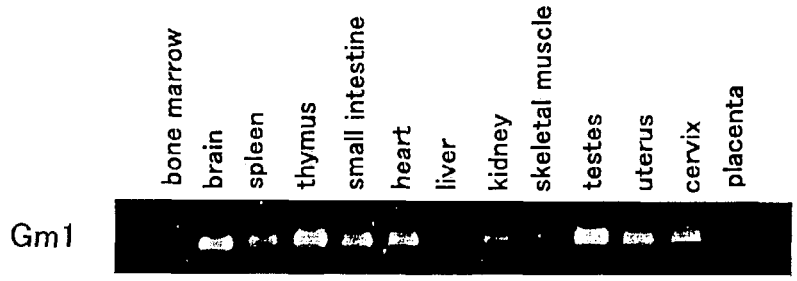
FIG. 1 is a drawing substitute showing the expression profile of an inventive protein in human tissues.

An inventive protein is a protein comprising any amino acid sequence selected from the group consisting of:
(a) The amino acid sequence represented by SEQ ID No:1;
(b) An amino acid sequence of a protein involved in a G protein-coupled receptor mediated signal transduction which consists of an amino acid sequence having a homology of 85% or more with the amino acid sequence represented by SEQ ID No:1;
(c) The amino acid sequence represented by SEQ ID No:25;
(d) The amino acid sequence represented by SEQ ID No:26;
(e) An amino acid sequence of a protein involved in a G protein-coupled receptor mediated signal transduction which comprises the amino acid sequence of the amino acid Nos. 96 to 126 of SEQ ID No:1;
(f) An amino acid sequence of a protein involved in a G protein-coupled receptor mediated signal transduction which comprises an amino acid sequence having a homology of 95% or more with the amino acid sequence of the amino acid Nos. 96 to 126 of SEQ ID No:1;
(g) An amino acid sequence of a protein involved in a G protein-coupled receptor mediated signal transduction which comprises at its N-terminal the amino acid sequence of the amino acid Nos. 1 to 126 of SEQ ID No:1; and
(h) An amino acid sequence of a protein involved in a G protein-coupled receptor mediated signal transduction which comprises at its N-terminal an amino acid sequence having a homology of 65% or more with the amino acid sequence of the amino acid Nos. 1 to 126 of SEQ ID No:1;

The inventive protein includes not only said protein but also its salt or derivative as long as its biological functions are not affected. A derivative is not limited particularly and may for example be one whose C terminal or other carboxyl group is converted into an amide, ester and the like, or one whose N terminal or other amino group is protected for example by a formyl group or acyl group. As a salt, an acid addition salt is exemplified preferably. An acid addition salt may for example be a salt with an inorganic acid such as hydrochloric acid, phosphoric acid, sulfuric acid and the like, or a salt with an organic acid such as formic acid, acetic acid, propionic acid and the like.

<First Protein>

The first protein according to the invention is a protein (1) or (2) shown below.

(1) The protein consisting of the amino acid sequence represented by SEQ ID No:1.
(2) A protein involved in a G protein-coupled receptor mediated signal transduction which consists of an amino acid sequence having a homology of 85% or more with the amino acid sequence represented by SEQ ID No:1.

The amino acid sequence represented by SEQ ID No:1 comprises an amino acid sequence part having a high homology with the GTP binding site and the GTPase activation site conserved among G protein α subunits. Such parts are the regions of the amino acid Nos. 126 to 133, 287 to 292, 353 to 359, 428 to 435 in the amino acid sequence represented by SEQ ID No:1. Any of these amino acids is in agreement with the GTP binding site and the GTPase activation site of Gs and Golf which has already been identified as G protein α subunits (NATURE, 117-127, 1991, vol. 349).

Furthermore, the amino acid also comprises a sequence which is identical to the characteristic sequence conserved highly in Gs and Golf protein belonging especially to the Gs family among the G protein α subunits (amino acid Nos. 119 to 126 in SEQ ID No:1), and can also form an α helix structure conserved among the G protein α subunits.

Based on these findings, the protein comprising the amino acid sequence represented by SEQ ID No:1 is considered to be a G protein α subunit.

The fact that a protein (2) functions as a molecule involved in the intracellular signal transduction by a GPCR stimulation can be verified by means of a screening method according to the invention discussed below.

The amino acid sequence of a protein (2) preferably has a homology of 90% or more, especially 95% or more with the amino acid sequence represented by SEQ ID No:1.

An index indicating which and how many amino acid residues in a protein (2) can be substituted, deleted or added without losing any biological functions can be identified for example by a GTP binding level assay described below. A variation causing no loss of the biological functions can be conducted for example in a part having a low homology with the amino acid sequence of any of various G protein α subunits which have already been identified.

In the case for example of an amino acid substitution, the amino acid can be substituted by an amino acid having the characteristics similar to those of the former amino acid in terms of polarity, electric charge, solubility, hydrophilicity/hydrophobicity, polarity and the like, in view of the maintenance of the protein structure. In this context, glycine, alanine, valine, leucine, isoleucine and proline are classified into non-polar amino acids; serine, threonine, cysteine, methionine, asparagine and glutamine are classified into polar amino acids; phenylalanine, tyrosine and tryptophane are classified into aromatic side chain-carrying amino acids; lysine, arginine and histidine are classified into basic amino acids; aspartic acid and glutamic acid are classified into acidic amino acids. Accordingly, the substitution may be conducted using an amino acid selected from the same group.

A protein (2) also includes proteins derived from other species corresponding to the human protein. Such an other species-derived corresponding protein can be deduced from a nucleotide sequence identified by means for example of a screening of a gene library of other species using a full length inventive polynucleotide or a part thereof as well as a 5'-RACE. Otherwise, a deductive identification is possible also from a corresponding gene of other species screened by an NCBI Blast search described below, A protein (2) may for example be the protein consisting of the amino acid sequence represented by SEQ ID No:25 and the protein consisting of the amino acid sequence represented by SEQ ID No:26.

<Second Protein>

The second protein according to the invention is a protein (3) or (4) shown below.
(3) A protein involved in a G protein-coupled receptor mediated signal transduction which comprises the amino acid sequence of the amino acid Nos. 96 to 126 of SEQ ID No:1.
(4) A protein involved in a G protein-coupled receptor mediated signal transduction which comprises an amino acid sequence having a homology of 95% or more with the amino acid sequence of the amino acid Nos. 96 to 126 of SEQ ID No:1.

A protein (4) preferably has a homology of 96% or more, especially 97% or more with the amino acid Nos. 96 to 126 in the amino acid sequence represented by SEQ ID No:1.

For the purpose of functioning as a molecule involved in an intracellular signal transduction by a GPCR stimulation, for example, as a G protein α subunit, each of the protein (3) and (4) usually has an amino acid sequence of the amino acid Nos. 75 to 133, 287 to 292, 353 to 359 and 428 to 435 in the amino acid sequence represented by SEQ ID No:1, or preferably has an amino acid sequence having a homology usually of 80% or more, especially 90% or more with the amino acid sequence of these regions. The total amino acid number is usually about 320 to 489, preferably about 350 to 460.

An index indicating which and how many amino acid residues in a protein (4) can be substituted, deleted or added without losing any biological functions of the protein (3) can be identified for example by a GTP binding level assay described below. A variation causing no loss of the biological functions can be conducted for example in a part having a low homology with the amino acid sequence of any of various G protein α subunits which have already been identified. Also similarly to the first protein described above, the substitution of a base can be conducted so that the amino acid obtained after a translation can possess the characteristics analogous to those of the amino acid before the substitution, with regard to polarity, electric charge, solubility, hydrophilicity/hydrophobicity, polarity and the like.

<Third Protein>

The third protein of the invention is a protein (5) or (6) shown below.
(5) A protein involved in a G protein-coupled receptor mediated signal transduction which comprises at its N-terminal of the amino acid sequence of the amino acid Nos. 1 to 126 of SEQ ID No:1.
(6) A protein involved in a G protein-coupled receptor mediated signal transduction which comprises at its N-terminal of an amino acid sequence having a homology of 65% or more with the amino acid sequence of the amino acid Nos. 1 to 126 of SEQ ID No:1.

In a protein (6), the amino acid sequence part corresponding to the 126 amino acid sequence at the N terminal of the protein (5) (hereinafter referred to as a "specific N terminal amino acid sequence") preferably has a homology of 70% or more, especially 75% or more with the specific N terminal amino acid sequence of the protein (5).

For the purpose of functioning as a molecule involved in an intracellular signal transduction by a GPCR stimulation, for example, as a G protein α subunit, each of the protein (5) and (6) usually has an amino acid sequence of the amino acid Nos. 75 to 133, 287 to 292, 353 to 359 and 428 to 435 in the amino acid sequence represented by SEQ ID No:1, or preferably has an amino acid sequence having a homology usually of 80% or more, especially 90% or more with these regions. The total amino acid number is usually about 320 to 480, preferably about 350 to 460.

An index indicating which and how many amino acid residues in a protein (6) can be substituted, deleted or added without losing any biological functions of the protein (5) can be identified for example by a GTP binding level assay described below. A variation causing no loss of the biological functions can be conducted for example in a part having a low homology with the amino acid sequence of any of various G protein α subunits which have already been identified. Also similarly to the first protein described above, the substitution of a base can be conducted so that the amino acid obtained after a translation can possess the characteristics analogous to those of the amino acid before the substitution, with regard to polarity, electric charge, solubility, hydrophilicity/hydrophobicity, polarity and the like.

There is no known G protein α subunit having the amino acid sequence of the amino acid Nos. 1 to126 of the amino acid sequence represented by SEQ ID No:1 or a sequence analogous thereto.

<Inventive Protein Production Method>

A protein of the invention can be produced by i) a method for separating a membrane fraction containing said protein from a cell or tissue of a human or other animal species followed by a known protein purification process, ii) a method employing a transformant of the invention described below or iii) a known chemical synthesis of a protein and the like.

In a method i), a cell or tissue of a mammalian animal including a human can be employed without limitation. It is particularly preferred to use a human cell or tissue, especially, a human brain-, uterus- or heart-derived cell or tissue.

A membrane fraction containing a protein of the invention can be obtained by suspending a cell or tissue for example in a HE/PI buffer (20 mM Hepes, 2 mM EDTA, 1× Proteinase inhibitor cocktail (Nacalaitesque)), pulverizing or lysing the suspension by means for example of an ultrasonic treatment, homogenization, passage through a needle of about 26 gauge, centrifuging the resultant pulverization or lysis solution at about 100 to 150×G for 5 to 10 minutes, centrifuging the resultant supernatant at about 18,000 to 20,000 G for 20 to 30 minutes, and then recovering the pellets.

The fact that the resultant cell membrane fraction contains a protein of the invention can be verified for example by a Western blotting using an antibody of the invention as described below.

A known protein purification method may for example be any of various chromatographic procedure such as an ion exchange, gel filtration, affinity chromatography. As a method iii), a method described for example in "The Peptide", Academic Press, New York (1966) or a method employing a commercial protein synthesis resin may be exemplified.

It is also possible to obtain a protein (2) from a transformant having a variant DNA which is formed by imparting a DNA encoding the protein (1) with a variation using a known method such as one described in Molecular Cloning: A Laboratory Manual, 2nd edition, Vol. 1 to 3, Cold Spring Harbor Laboratory Press (1989), Methods in Enzymology p448 (1989), PCR A Practical Approach IRL Press p200 (1991) and the like, for example, a site-specific mutation introduction, a PCR employing a variation primer. This may analogously be applied to a method for obtaining the protein (3) from a protein (4) and a method for obtaining the protein (6) from a protein (5).

<Application of Inventive Proteins>

A protein of the invention can preferably be employed as a regulator of a signal transduction mediated by a GPCR stimulation. Specifically, it can preferably be employed for treating or preventing a disease associated with an intracellular signal transduction relating to the defect, reduced expression level or reduced function of a protein of the invention.

<Inventive Polynucleotide>

A polynucleotide according to the invention is a polynucleotide encoding a protein of the invention described above, and comprises a nucleotide sequence selected from the group consisting of:

(a) A nucleotide sequence encoding the amino acid sequence represented by SEQ ID No:1;

(b) A nucleotide sequence encoding an amino acid sequence of a protein involved in a G protein-coupled receptor mediated signal transduction which consists of an amino acid sequence having a homology of 85% or more with the amino acid sequence represented by SEQ ID No:1;

(c) A nucleotide sequence encoding the amino acid sequence represented by SEQ ID No:25;

(d) A nucleotide sequence encoding the amino acid sequence represented by SEQ ID No:26;

(e) A nucleotide sequence encoding an amino acid sequence of a protein involved in a G protein-coupled receptor mediated signal transduction which comprises the amino acid sequence of the amino acid Nos. 96 to 126 of SEQ ID No:1;

(f) A nucleotide sequence encoding an amino acid sequence of a protein involved in a G protein-coupled receptor mediated signal transduction which comprises an amino acid sequence having a homology of 95% or more with the amino acid sequence of the amino acid Nos. 96 to 126 of SEQ ID No:1;

(g) A nucleotide sequence encoding an amino acid sequence of a protein involved in a G protein-coupled receptor mediated signal transduction which comprises at its N-terminal the amino acid sequence of the amino acid Nos. 1 to 126 of SEQ ID No:1;

(h) A nucleotide sequence encoding an amino acid sequence of a protein involved in a G protein-coupled receptor mediated signal transduction which comprises at its N-terminal an amino acid sequence having a homology of 65% or more with the amino acid sequence of the amino acid Nos. 1 to 126 of SEQ ID No:1;

(i) The nucleotide sequence represented by SEQ ID No:2;

(j) A nucleotide sequence encoding a protein involved in a G protein-coupled receptor mediated signal transduction which is a nucleotide sequence having a homology of 85% or more with the polynucleotide consisting of the nucleotide sequence represented by SEQ ID No:2;

(k) The nucleotide sequence represented by SEQ ID No:27;

(l) The nucleotide sequence represented by SEQ ID No:28;

(m) A nucleotide sequence encoding a protein involved in a G protein-coupled receptor mediated signal transduction which comprises the nucleotide sequence of the nucleotide Nos. 289 to 378 of SEQ ID No:2;

(n) A nucleotide sequence encoding a protein involved in a G protein-coupled receptor mediated signal transduction which comprises a nucleotide sequence having a homology of 90% or more with the polynucleotide consisting of the nucleotide sequence of the nucleotide Nos. 289 to 378 of SEQ ID No:2;

(o) A nucleotide sequence encoding a protein involved in a G protein-coupled receptor mediated signal transduction which comprises at its 5' terminal the nucleotide sequence of the nucleotide Nos. 1 to 378 of SEQ ID No:2; and (p) A nucleotide sequence encoding a protein involved in a G protein-coupled receptor mediated signal transduction which comprises at its 5' terminal a nucleotide sequence having a homology of 70% or more with the polynucleotide consisting of the nucleotide sequence of the nucleotide Nos. 1 to 378 of SEQ ID No:2.

A polynucleotide of the invention (including an oligonucleotide) includes a polynucleotide comprising a nucleotide sequence described above and a polynucleotide complementary thereto. Unless otherwise specified, a polynucleotide includes the both of a DNA and an RNA. A DNA includes a single-stranded DNA having its nucleotide sequence, and a single-stranded DNA complementary thereto, and a double-stranded DNA. A DNA, unless otherwise specified, includes a cDNA, genome DNA and synthetic DNA. An RNA, unless otherwise specified, includes a total RNA, mRNA, rRNA and synthetic RNA.

An inventive polynucleotide is detailed with referring to the following first, second and third polynucleotide described below.

<First Polynucleotide>

(7) The polynucleotide consisting of the nucleotide sequence represented by SEQ ID No:2.

(8) A polynucleotide encoding a protein involved in a G protein-coupled receptor mediated signal transduction which consists of a nucleotide sequence having a homology of 85% or more with the polynucleotide consisting of the nucleotide sequence represented by SEQ ID No:2.

A polynucleotide (8) preferably has a homology of 87% or more, especially 90% or more with the polynucleotide (7).

A polynucleotide (8) is preferably one which hybridizes under a stringent condition with the polynucleotide (7) consisting of the nucleotide sequence represented by SEQ ID No:2. In the invention, a stringent condition may for example be a condition involving 2×SSC, 1× Denhart's solution at about 60° C.

An index indicating which and how many bases in a polynucleotide (8) can be substituted, deleted or added without losing any biological functions of the protein encoded by the polynucleotide (7) can be identified for example by a cAMP assay or a GTP binding level assay described below. A variation causing no loss of the biological functions can be conducted for example in a part having a low homology with the polynucleotide sequence of any of various G protein α subunits which have already been identified.

Also similarly to the first protein described above, the substitution of a base can be conducted so that the amino acid obtained after a translation can possess the characteristics analogous to those of the amino acid before the substitution, with regard to polarity, electric charge, solubility, hydrophilicity/hydrophobicity, polarity and the like.

When a single amino acid has several translation codons, the base substitution within these translation codons may also be possible. For example, when alanine has 4 translation codons, namely, GCA, GCC, GCG and GCT, the third base in each codon can be substituted with each other among ATGC.

A polynucleotide (8) includes a polynucleotide of other species corresponding, for example, to a human polynucleotide. Such a polynucleotide can be screened for using NCBI blast search. Typically, a nucleotide sequence containing the nucleotide residues 289 to 378 of SEQ ID No:2 is subjected to an NCBI blast search to thereby search the nucleotide sequence database of other species and an EST database for a sequence having a high homology. By screening the nucleotide sequences selected by the search for a nucleotide sequence whose region corresponding to the nucleotide residues 289 to 378 has a homology for example of 90% or more, a corresponding gene of other species can be screened for.

A polynucleotide (8) is preferably one whose nucleotide sequence corresponding to the nucleotide Nos. 1 to 222, 400 to 858, 877 to 1056, 1078 to 1281 and 1306 to 1377 in SEQ ID No:2 in the polynucleotide (7) has a homology usually of 75% or more, especially 80% or more with the respective nucleotide sequence of the polynucleotide (7).

A polynucleotide (8) may for example be a polynucleotide consisting of the nucleotide sequence represented by SEQ ID No:27 and a polynucleotide consisting of the nucleotide sequence represented by SEQ ID No:28.

<Second Polynucleotide>

(9) A polynucleotide encoding a protein involved in a G protein-coupled receptor mediated signal transduction which comprises the nucleotide sequence of the nucleotide Nos. 289 to 378 of SEQ ID No:2.

(10) A polynucleotide encoding a protein involved in a G protein-coupled receptor mediated signal transduction which comprises a nucleotide sequence having a homology of 90% or more with the polynucleotide consisting of the nucleotide sequence of the nucleotide Nos. 289 to 378 of SEQ ID No:2.

In a polynucleotide (10), the nucleotide sequence corresponding to the nucleotide Nos. 289 to 378 in SEQ ID No:2 of a polynucleotide (9) has a homology of 93% or more, especially 95% or more with the respective sequence of (9).

A polynucleotide (10) preferably has a polynucleotide sequence which hybridizes under a stringent condition with a polynucleotide consisting of the nucleotide sequence of the nucleotide Nos. 289 to 378 in SEQ ID No:2.

Each of the protein (9) and (10), for achieving the function of the protein encoded thereby as a molecule involved in an intracellular signal transduction by a GPCR stimulation, for example, as a G protein α subunit, usually has a nucleotide sequence of the nucleotide Nos. 223 to 399, 859 to 876, 1057 to 1077, 1282 to 1305 in the nucleotide sequence represented by SEQ ID No:2, or preferably has an nucleotide sequence having a homology usually of 85% or more, especially 90% or more with these regions. The total nucleotide number is usually about 963 to 1443, especially 1053 to 1383.

An index indicating which and how many bases in a polynucleotide (10) can be substituted, deleted or added without losing any biological functions of the protein encoded by the polynucleotide (9) is similar to that described above with regard to the first polynucleotide.

<Third Polynucleotide>

(11) A polynucleotide encoding a protein involved in a G protein-coupled receptor mediated signal transduction which comprises at its 5' terminal the nucleotide sequence of the nucleotide Nos. 1 to 378 of SEQ ID No:2.

(12) A polynucleotide encoding a protein involved in a G protein-coupled receptor mediated signal transduction which comprises at its 5' terminal a nucleotide sequence having a homology of 70% or more with the polynucleotide consisting of the nucleotide sequence of the nucleotide Nos. 1 to 378 of SEQ ID No:2.

In a polynucleotide (12), the nucleotide sequence part corresponding to the 378 nucleotide sequence at the 5' terminal of the protein (11) (hereinafter referred to as a "specific 5' terminal nucleotide sequence") preferably has a homology of 75% or more, especially 80% or more with the specific 5' terminal amino acid sequence of (11).

A polynucleotide (12) preferably has at its 5' terminal a polynucleotide sequence which hybridizes under a stringent condition with the polynucleotide consisting of the nucleotide sequence of the nucleotide Nos. 1 to 378 in SEQ ID No:2.

Each of the protein (11) and (12), for achieving the function of the protein encoded thereby as a molecule involved in an intracellular signal transduction by a GPCR stimulation, for example, as a G protein α subunit, usually has a nucleotide sequence of the nucleotide Nos. 223 to 399, 859 to 876, 1057 to 1077, 1282 to 1305 in the nucleotide sequence represented by SEQ ID No:2, or preferably has an nucleotide sequence having a homology usually of 85% or more, especially 90% or more with these regions. The total nucleotide number is usually about 963 to 1443, especially 1053 to 1383.

An index indicating which and how many bases in a polynucleotide (12) can be substituted, deleted or added without losing any biological functions of the protein encoded by the polynucleotide (11) is similar to that described above with regard to the first polynucleotide.

There is no polynucleotide encoding a G protein α subunit having the nucleotide sequence of the nucleotide Nos. 1 to 378 in SEQ ID No:2 or a sequence analogous thereto.

<Inventive Polynucleotide Production Method>

Polynucleotides (7) to (12) can be obtained for example by a screening a human DNA library by a hybridization using as a probe an oligonucleotide (for example, an oligonucleotide of the invention described below) synthesized based on the nucleotide sequence represented by SEQ ID No:2. They can be obtained also by a PCR in a standard manner after preparing suitable primers (for example, oligonucleotides of the invention described below) based for example on the nucleotide sequence of SEQ ID No:2 using as a PCR template a cDNA library for example of a human, rat and mouse. They can be obtained also by a chemical synthesis.

As a cDNA library, one derived from a brain, thymus, testes, spleen, small intestine, uterus and heart is preferred.

A method for obtaining a polynucleotide (10) by introducing a variation into a polynucleotide (9) and a method for obtaining a polynucleotide (12) by introducing a variation into a polynucleotide (11) are as described above.

<Application of Inventive Polynucleotide>

An inventive polynucleotide can be used preferably as a regulator of an intracellular signal transduction mediated by a GPCR stimulation. Typically, it can be used preferably for treating or preventing a disease caused by an abnormality in this intracellular signal transduction. It is useful especially in treating or preventing a disease associated with an intracellular signal transduction relating to the defect, reduced expression level or reduced function of a protein of the invention.

An inventive polynucleotide can be used preferably also in screening for a substance capable of regulating a signal transduction mediated by a GPCR and a G protein of the invention.

<Inventive Recombinant Vector and Transformant>

An inventive recombinant vector is a vector containing an inventive polynucleotide (which herein is a DNA). For example, it may be a vector capable of expressing a protein of the invention.

A vector capable of expressing a protein of the invention can be produced by ligating an inventive polynucleotide to an expressible position downstream of a promoter of an expression vector in accordance with a standard method.

An expression vector may be selected from known vectors capable of replicating in host cells as appropriate depending on the host cells. For example, a pBR322, pUC12, pUC119 and pBluescript can be exemplified when an E.coli is employed as a host cell, while a pUB110 and pC194 are exemplified when a Bacillus organism is employed as a host cell. An Yip5 and Yep24 are exemplified when using an yeast as a host cell. An AcNPV is exemplified when using an insect cell as a host cell. A pUC18 and pUC19 are exemplified when using an animal cell as a host cell.

A host cell may be any of those known in the art without limitation. Those which may be exemplified are bacteria such as an E.coli (for example, K12) and a Bacillus microorganism (for example, MI114), yeasts (for example, AH22), insect cells (for example, Sf cell), animal cells (for example, COS-7 cell, Vero cell, CHO cell and the like).

A method for transforming a host cell with an inventive recombinant vector may be a known method selected suitably depending on the host cell. A known introduction method may for example be a calcium phosphate method, electroporation, lipofection, DEAE dextran method and the like. From transformants, an inventive transformant is selected for example by means of a drug resistance marker possessed by the vector as an index.

<Inventive Protein Production Method>

A method for producing a protein of the invention is a method in which an inventive transformant is cultured and an inventive protein is recovered from the resultant culture product.

The conditions of culturing a transformant may be selected appropriately depending on the type of the transformant.

When an inventive transformant is a microorganism, the culture is conducted in a liquid medium or plate medium employed usually for culturing a microorganism. The culture temperature may be within the range allowing a microorganism to be grown, for example from 15 to 40° C. The culture medium pH may also be within the range allowing a microorganism to be grown, for example about pH6 to 8. The culture time period may vary depending on other culturing conditions, and may usually be 1 to 5 days, especially 1 to 2 days. When using an inducible expression vector such as those of the temperature shift type or IPTG inducible type, the induction time period may be within a day, especially within several hours.

Also when an inventive transformant is a mammalian cell, it can be cultured under the condition suitable for said cell. For example, an FBS-supplemented DMEM medium (NISSUI) may be employed to conduct a culture in the presence of 5% $CO_2$ at a temperature of 36 to 38° C. with replacing the medium with a fresh one at an interval of several days. Upon confluent growth, the cells were combined with a trypsin PBS solution to disperse into individual cells and the resultant cell suspension was diluted by several times and inoculated onto a new petri dish, which is then subjected to a subculture. The culture time period is usually 2 to 5 days, especially 2 to 3 days.

Also when an insect cell is employed as a transformant, the culture condition may be adjusted appropriately depending on the type of the cell. For example, an insect cell culture medium such as Grace's medium containing FBS and Yeastlate may be employed to conduct the culture at 25 to 35° C. The culture time period is 1 to 5 days, especially 2 to 3 days. When using as a vector an virus-containing transformant such as a Baculovirus, the culture is continued preferably until the time before the cell death as a result of the onset of the cytoplasmic effect (for example, 3 to 7 days, especially 4 to 6 days).

After completion of the culture, the transformant cells were recovered by a centrifugation, suspended in a suitable buffer if desired, and dispersed by means of a polytron, ultrasonic treatment, homogenizer and the like. The resultant dispersion is centrifuged at about 100 to 150 G for about 5 to 10 minutes, and the resultant supernatant is centrifuged at about 18,000 to 20,000 G for about 20 to 30 seconds to recover the pellet, whereby obtaining a cell membrane fraction.

The cell membrane fraction thus obtained is subjected to a known protein purification method, such as any of chromatographic methods including ion exchange, hydrophobic, gel filtration and affinity chromatographies, whereby purifying the protein according to the invention.

An inventive protein can be expressed for example as being attached with a histidine tag, or as a glutathion S transferase fusion protein. The former case employs a metal chelate affinity column, while the latter case employs a glutathion S transferase monoclonal antibody column, whereby accomplishing the purification of an inventive protein in a further convenient manner.

<Inventive Anti Sense Polynucleotide>

<Aspect>

An inventive antisense polynucleotide is a polynucleotide (13) or (14) shown below.

(13) A polynucleotide which inhibits expression of a protein of the invention which consists of a nucleotide sequence complementary to at least 15 contiguous nucleotides in the nucleotide sequence represented by SEQ ID No:2.

(14) A polynucleotide which inhibits expression of a protein of the invention which hybridizes under an intracellular condition with a polynucleotide consisting of at least 15 contiguous nucleotides in the nucleotide sequence represented by SEQ ID No:2.

An antisense oligonucleotide of the invention hybridizes with a mRNA encoding an inventive protein to inhibit the translation from the mRNA to the protein or cleaves the mRNA, whereby inhibiting the expression of this protein.

While the upper limit of the number of the nucleotides in an antisense polynucleotide is not limited particularly, it is usually about 60 nucleotides for the purpose of achieving the objective.

A polynucleotide (13) preferably has a nucleotide sequence complementary to at least 30 nucleotides, especially at least 50 nucleotides in the polynucleotide represented by SEQ ID No:2. An antisense (14) is preferably one which hybridizes under an intracellular condition also with a polynucleotide consisting of at least 30 nucleotides, especially at least 50 nucleotides in the polynucleotide represented by SEQ ID No:2.

A polynucleotide which hybridizes under an intracellular condition in the invention may for example be a polynucleotide which hybridizes under a stringent condition described below. The stringent condition may for example be a condition involving 2×SSC, 1× Denhart's solution at about 60° C.

A polynucleotide (13) preferably has a nucleotide sequence complementary to at least 15 contiguous nucleotides across the both of the region of the nucleotide Nos. 1 to 378 and the region of the nucleotide Nos. 379 to 1377 in SEQ ID No:2.

Similarly, a polynucleotide (14) is preferably one which hybridizes under an intracellular condition with a polynucleotide consisting of at least 15 contiguous nucleotides across the both of the region of the nucleotide Nos. 1 to 378 and the region of the nucleotide Nos. 379 to 1377 in SEQ ID No:2.

"At least 15 contiguous nucleotides in the nucleotide sequence represented by SEQ ID No:2" in polynucleotides (13) and (14) which is closer to the 5' terminal of SEQ ID NO:2 is more preferable.

An antisense polynucleotide of the invention may be a single-stranded DNA, double-stranded DNA, single-stranded RNA, double-stranded RNA or DNA•RNA hybrid. When a double-stranded RNA is employed, it is generally called an RNAi. A derivative of such a nucleotide may also be employed as long as it inhibits the expression of an inventive protein. A derivative may for example be a phosphorthioate DNA, H-phosphonate DNA and the like.

Inhibition of an inventive protein expression by an inventive antisense polynucleotide can be verified for example by a method described below. A human brain-derived cell is combined with an antisense at about 5 nM to 10 µM if necessary together with a known intracellular introduction reagent such as a lipofection reagent, lipofectamine reagent, liposome and the like. Then, from this cell a cell extract is prepared by a known method and an inventive antibody is used to measure expression level of the inventive protein by a known method such as an ELISA or western blotting. This expression level is compared with the level observed in the absence of the antisense.

An inventive antisense polynucleotide may for example be one which reduces the inventive protein expression level for example to 70% or less, preferably to 50% or less based on the level in the absence of the antisense polynucleotide.

An inventive antisense polynucleotide can be produced by a known chemical synthesis method.

<Application of Antisense Polynucleotide>

An inventive antisense polynucleotide can be used preferably as a regulator of an intracellular signal transduction mediated by a GPCR stimulation. Typically, it can be used preferably for treating or preventing a disease caused by an abnormality in this intracellular signal transduction. It is useful preferably for the purpose especially of suppressing the increased abnormality in this intracellular signal transduction.

<Ribozyme>

<Aspect>

An inventive ribozyme is a ribozyme (15) or (16) shown below.

(15) A ribozyme having an ability of cleaving a polynucleotide of the invention which comprises two polynucleotide regions complementary to two regions respectively consisting of at least 9 contiguous nucleotides which are two regions in the nucleotide sequence represented by SEQ ID No:2.

(16) A ribozyme having an ability of cleaving a polynucleotide of the invention which comprises two polynucleotide regions which hybridizes under an intracellular condition with two regions respectively consisting of at least 9 contiguous nucleotides which are two regions in the nucleotide sequence represented by SEQ ID No:2.

A ribozyme (15) preferably comprises two polynucleotide regions complementary to two regions respectively consisting of at least 10, especially 11 contiguous nucleotides which are two regions in the nucleotide sequence represented by SEQ ID No:2.

A ribozyme (16) preferably,comprises two polynucleotide regions which hybridizes under an intracellular condition with two regions respectively consisting of at least 10, especially 11 contiguous nucleotides which are two regions in the nucleotide sequence represented by SEQ ID No:2.

In the ribozymes (15) and (16), the two regions in the nucleotide sequence represented by SEQ ID No:2 may be adjacent to each other, or but may preferably be interrupted by about 1 to 4 nucleotides present between them. For example, a hammer-head ribozyme may contain a single interrupting nucleotide, while a hairpin ribozyme may contain 4 interrupting nucleotides.

A ribozyme is an RNA molecule containing an antisense sequence recognizing a specific site of an RNA, and has an RNA cleavage enzyme activity. As a result, the ribozyme recognizes its target RNA, and cleaves a certain site of the RNA specifically.

An inventive ribozyme may be of a hammer-head or hairpin type. A hammer-head type usually recognize an NUX (N is G, U, C or A, while X is C, U or A) and cleaves a mRNA at the 3'-position of the X.

A hammer-head ribozyme according to the invention may for example be a ribozyme comprising a nucleotide sequence listed below.

A ribozyme comprising the nucleotide sequence:

(SEQ ID No:3)
UCGCCUCCUUCUGAUGAGGCCCGAAGGCCGAAACCGCCUCGCGC.

The ribozyme having this nucleotide sequence once forms its conformation and then recognizes the nucleotide sequence of the nucleotide Nos. 273 to 295 in SEQ ID No: 2.

A ribozyme comprising the nucleotide sequence:

(SEQ ID No:4)
CGGCCGCCCGCUGAUGAGGCCGAAAGGCCGAAACUGGGGCCAGC.

The ribozyme having this nucleotide sequence once forms its conformation and then recognizes the nucleotide sequence of the nucleotide Nos. 111 to 133 in SEQ ID No: 2.

A ribozyme comprising the nucleotide sequence:

(SEQ ID No:5)
CAGCGGCCGCCUGAUGAGGCCGAAAGGCCGAAACUGUAGCACA.

The ribozyme having this nucleotide sequence once forms its conformation and then recognizes the nucleotide sequence of the nucleotide Nos. 8 to 30 in SEQ ID No: 2.

A hairpin type ribozyme usually recognizes an NNNG/CN*GUCNNNNNNNN (N is G, U, C or A), and cleaves a mRNA between N*G.

A hairpin ribozyme according to the invention may for example be a ribozyme comprising a nucleotide sequence listed below.

A ribozyme comprising the nucleotide sequence:

(SEQ ID No:6)
UCGCCUCCUUAGAAGCCUACCAGAGAAACACACGUUGUGGUAUAUUACCUG GUA.

The ribozyme having this nucleotide sequence once forms its conformation and then recognizes the nucleotide sequence of the nucleotide Nos. 287 to 295 in SEQ ID No: 2.

A ribozyme comprising the nucleotide sequence:

(SEQ ID No:7)
CGGCCGCCCGAGAAGGGGACCAGAGAAACACACGUUGUGGUAUAUUACCU GGUA.

The ribozyme having this nucleotide sequence once forms its conformation and then recognizes the nucleotide sequence of the nucleotide Nos. 116 to 133 in SEQ ID No: 2.

A ribozyme comprising the nucleotide sequence:

(SEQ ID No:8)
CAGCGGCCGCAAGAAGUAGACCAGAGAAACACACGUUGUGGUAUAUUACCU GGUA.

The ribozyme having this nucleotide sequence once forms its conformation and then recognizes the nucleotide sequence of the nucleotide Nos. 12 to 30 in SEQ ID No: 2.

While an inventive ribozyme usually consists of an RNA, a one which includes a deoxyribonucleotide or a derivative such as a phosphorthioate DNA which is difficult to be decomposed in vivo are also included in the inventive ribozyme.

An inventive ribozyme can be produced by a known chemical synthesis method, in vitro or in vivo transcription and the like. Typically, an in vitro transcription involves the ligation of a DNA having a sequence complementary to the sequence of SEQ ID No:3, 4, 5, 6, 7 or 8 to the downstream of the DNA encoding a promoter such as T7, T3 or SP6. Using this DNA as a template, a transcription reaction by an RNA polymerase is conducted. The resultant transcription product can be used as an RNA for the ribozyme.

An in vivo transcription involves the integration of a DNA having a sequence complementary to the sequence of SEQ ID No:3, 4, 5, 6, 7 or 8 into an mammalian expression vector followed by the transduction of this expression vector into a mammalian cell. As a result of the cellular transcription mechanism, an RNA having the sequence of SEQ ID No:3, 4, 5, 6, 7 or 8 is synthesized.

<Application of Ribozyme>

An inventive ribozyme can be used preferably as a regulator of an intracellular signal transduction mediated by a GPCR stimulation. Typically, it can be used preferably for treating or preventing a disease caused by an abnormality in this intracellular signal transduction. It is useful preferably for the purpose especially of suppressing the increased abnormality in this intracellular signal transduction.

<Inventive Antibody>

<Aspect>

An inventive antibody is an antibody which recognizes an inventive protein specifically. The inventive antibody may be a polyclonal antibody or monoclonal antibody. The inventive antibody includes an antibody having an antigen binding ability toward a polypeptide consisting of 5 contiguous amino acids, preferably 10 amino acids in the amino acid sequence constituting an inventive protein. In addition, a derivative of such an antibody (chimera antibody and the like) or a one labeled with an enzyme such as a peroxidase are also included in the inventive antibody.

<Method for Producing Inventive Antibody>

Any of the antibodies described above can be produced in accordance with a known production method (for example, Current protocols in Molecular Biology edit. Ausubel et al. (1987) Publish. John Wiley and Sons. Section 11.12-11.13).

Typically, when an inventive antibody is a polyclonal antibody, it can be obtained by immunizing a non-human animal such as a rodent animal with an inventive protein followed by the isolation from the serum of this immunized animal in accordance with a standard method. When an inventive antibody is a monoclonal antibody, it can be obtained from a hybridoma produced by immunizing a non-human animal such as a mouse with a polypeptide having an inventive protein or its partial sequence followed by fusing the spleen cell of this immunized animal with a myeloma cell (Current protocols in Molecular Biology edit. Ausubel et al. (1987) Publish. John Wiley and Sons. Section 11.4-11.11).

<Application of Antibody>

An inventive antibody can be used preferably as a regulator of an intracellular signal transduction mediated by a GPCR stimulation. Typically, it can be used preferably for treating or preventing a disease caused by an abnormality in this intracellular signal transduction. It is useful preferably for the purpose especially of suppressing the increased abnormality in this intracellular signal transduction.

An inventive antibody can preferably be used also in the affinity chromatography for purifying an inventive protein as well as in the screening for a substance which may affect the expression of an inventive protein.

<Inventive Oligonucleotide>

An inventive oligonucleotide is an oligonucleotide (17) or (18) shown below.

(17) An oligonucleotide capable of recognizing a polynucleotide represented by SEQ ID NO:2 specifically which consists of at least 17 contiguous nucleotides in the nucleotide sequence represented by SEQ ID No:2.

(18) An oligonucleotide capable of recognizing a polynucleotide represented by SEQ ID NO:2 specifically, which has a homology of 80% or more with at least 17 contiguous nucleotides in the nucleotide sequence represented by SEQ ID No:2.

The length of each of the oligonucleotides (17) and (18) can be selected appropriately depending on the use. It may be the full length of SEQ ID No:2.

An oligonucleotide (18) preferably has a homology of 85% or more, especially 90% or more with an oligonucleotide (17).

The expression "recognize specifically" in conjunction with oligonucleotides (17) and (18) means that each oligonucleotide can be employed to detect the nucleotide sequence represented by SEQ ID No:2 specifically or selectively by a known nucleotide sequencing means such as a northern blotting or PCR.

An inventive oligonucleotide can be used as a probe or primer which can detect or amplify an RNA generated as a result of the expression of an inventive DNA or a polynucleotide derived therefrom in a specific manner. Typically, it can be used as a probe or primer in a known method for detecting a certain nucleotide sequence, such as a Northern blotting, in situ hybridization or PCR.

As a result, the absence or presence of the expression of, or the expression level of an inventive polynucleotide can be assessed. Accordingly, an inventive oligonucleotide can preferably used for diagnosing a disease caused by a signal transduction abnormality resulting from the defect of and the abnormal increase or decrease in the expression level of the inventive protein. A test sample may be a total RNA prepared by a standard method from a sample taken from a tissue of a subject such as an uterus or any of various polynucleotides prepared from such an RNA.

An inventive oligonucleotide may for example be ones having the nucleotide sequences of

```
                                              (SEQ ID No:9)
5'-ATGGGTCTGTGCTACAGTCTGCGG
and
                                              (SEQ ID No:10)
5'-ACGATGGTGCTTTTCCCAGACTCACCAGCCCCGAGCA.
```

This oligonucleotide set can preferably used as PCR primers for amplifying a protein of the invention.

<Inventive Screening Method>

A polynucleotide of the invention can be used for screening for a substance which activates or inhibits (or suppress) the cellular signal transduction mediated by a GCPR and an inventive protein.

A GPCR stimulating signal is transmitted to an effector via the activation of a G protein as a result of the GDP/GTP exchange reaction on a G protein α subunit. Accordingly, by using the change in the activity of this effector as an index in screening test substances, a substance capable of activating or inhibiting the signal transduction mediated by a GPCR and a G protein α subunit can be identified. In addition, also by using the change in the level of the binding of a GTP to a membrane fraction of a cell expressing a G protein as an index in screening test substances, a substance capable of activating or inhibiting the signal transduction mediated by a GPCR and a G protein α subunit can be identified.

Otherwise, by screening test substances which alter the level of the expression of an inventive protein, a substance capable of activating or inhibiting the signal transduction mediated by a GPCR and a G protein α subunit can be identified.

<First Method>

A method for screening for a substance capable of regulating a signal transduction mediated by a GPCR and an inventive protein comprising:

(a) a step for bringing a test substance into contact with a test cell having a recombinant vector containing an inventive polynucleotide (which herein is a DNA encoding an inventive protein) and a recombinant vector containing a DNA encoding a GPCR;

(b) a step for measuring the G protein effector activity or the index value correlating therewith in the test cell (hereinafter abbreviated as "effector activity"); and (c) a step for comparing this effector activity with the effector activity in the test cell which has not been brought into contact with the test substance, whereby selecting a test substance capable of altering the effector activity in the test cell.

In the first method, an agonist of GPCR can be selected.

A cell in which a recombinant vector having a DNA encoding an inventive protein and a recombinant vector having a DNA encoding a GPCR are contained may for example be but not limited to a mammalian cell or insect cell. A mammalian cell may be any known cell such as a Vero cell, Hela cell, CV1 cell, COS1 cell, CHO cell and the like, which may be employed without limitation. An insect cell may be any known cell such as a Sf cell, MG1 cell, High Five™ cell, and the like, which may be employed without limitation. The type of the vector is not limited particularly, and any known vector may be selected depending on the type of the cell.

A DNA encoding a GPCR can be obtained by a method for screening a human cDNA library using a probe designed based on the nucleotide sequences described in a GPCR database (www.cmbi.kun.nl/7tm/), by a method for conducting a PCR using as a template a human cDNA library together with the primers designed based on the nucleotide sequences described above, or by a chemical synthesis method and the like.

An effector of a G protein may be an effector which is a target of a G protein α subunit or may be an effector which is a target of a G protein βγ subunit. It is also possible to measure an index value correlating with the effector activity of a G protein.

An effector which is targeted by a G protein α subunit may for example be an adenylate cyclase, $Ca^{2+}$ channel, $K^+$ channel, phospholipase Cβ and the like. The adenylate cyclase activity be assessed by measuring the intracellular cAMP level. The $Ca^{2+}$ channel activity can be assessed by measuring the cell membrane electric potential. The $K^+$ channel activity can be assessed by measuring the cell membrane electric potential. The phospholipase Cβ activity can be assessed by measuring the $Ca^{2+}$ level.

An effector which is targeted by a G protein βγ subunit may for example be an adenylate cyclase, $Ca^{2+}$ channel, $K^+$ channel, phospholipase Cβ, phosphatidyl inositol 3-kinase β or γ and the like. The phosphatidyl inositol 3-kinase β or γ activity can be assessed by measuring the $Ca^{2+}$ level.

An effector to be examined for its activity is preferably an effector targeted by a G protein α subunit, with an adenylate cyclase being more preferred. The intracellular cAMP level which reflects the adenylate cyclase activity can be measured by a known method such as an RIA employing an anti-cAMP antibody obtained by immunizing a mouse, rat, rabbit, goat, cattle and the like together with a $^{125}I$-labeled cAMP, other EIA employing a combination of an anti-cAMP antibody and a labeled cAMP, a SPA method employing a scintillant obtained by immobilizing an anti-cAMP antibody using a protein A or an antibody against an animal IgG used for producing an anti-cAMP antibody together with a $^{125}I$-labeled cAMP, an EFC method employing a combination of an anti-cAMP antibody, enzyme donor-binding cAMP and enzyme blank acceptor, and the like. Any of these measurements can be accomplished using a commercial kit.

An intracellular cAMP level can be assessed also by a method in which, for example, a CRE (cAMP response element, which reacts with a cAMP)-containing DNA is inserted into the upstream of the reporter gene of a reporter gene vector to form a CRE-reporter gene vector, and this vector is also introduced into a test cell and then the reporter gene expression level is measured. In a cell into which a CRE-reporter gene vector has been introduced, a stimulation accompanied with an elevation in the cAMP level induces a reporter gene expression mediated by the CRE and the subsequent reporter protein production. On the contrary, a reduction in the cAMP level leads to a reduction in the CRE-mediated reporter protein production. By using a CRE reporter gene vector, the cAMP level can be measured conveniently at a high sensitivity.

As a reporter gene, any of known genes can be employed without limitation, including a luciferase gene, secretor alkaline phosphatase (SEAP) gene, chloramphenicol acetyltransferase (CAT) gene, β-galactosidase gene and the like. Any of these genes can be examined for its expression level using a commercial measurement kit described below. The luciferase gene expression level can be measured by adding a luminescent substrate luciferrin (manufactured for example by TOYO INK) to a cell solution followed by measuring the luminescence resulting from the decomposition of the substrate using a luminometer, liquid scintillation counter or top counter. Expression level of the alkaline phosphatase gene can be determined for example by using LμMi-Phos530 (WAKO PURE CHEMICAL). Expression, level of the chloramphenicol acetyltransferase gene can be determined using a FAST CAT Chloramphenicol Acetyltransferase Assay Kit (WAKO PURE CHEMICAL). Expression level of the β-galactosidase gene can be determined using an AURORA Gal-XE (WAKO PURE CHEMICAL).

In the case for example where a luciferase gene is employed, a CRE-containing DNA is inserted into a multiple cloning site in the upstream of a luciferase gene such as a PICK-A-GENE Basic Vector or a PICK-A-GENE Enhancer vector (TOYO INK) and the like, which is then used as a CRE reporter gene vector.

The type of a test substance is not limited particularly. Those which may be exemplified are proteins, peptides, non-peptide compounds (nucleotides, amines, saccharides, lipids and the like), organic low molecular compounds, inorganic low molecular compounds, fermentation products, cell extracts, plant extracts, animal tissue extracts and the like.

The contact of a cell with a test substance may be effected under a condition avoiding the cell death and allowing an inventive protein and a GPCR to be expressed from an introduced vector (temperature, pH, medium composition). The concentration of a test substance upon contact with a cell may for example be about 0.001 to 10 μM, although it may vary depending on the type of the substance.

A test substance which increase the effector activity of a test cell brought into contact with the test substance for example by about 25%, preferably about 50%, more preferably about 100%, when com pared with the effector activity in the test cell which was not brought into contact with the test substance, can be selected as a GPCR agonist.

<Second Method>

A method for screening for a substance capable of regulating a signal transduction mediated by a GPCR and an inventive protein comprising:

(a) a step for bringing a test substance into contact with a test cell having a recombinant vector containing an inventive polynucleotide (which herein is a DNA encoding an inventive protein) and a recombinant vector containing a DNA encoding a GPCR;

(b) a step for measuring the G protein effector activity in the test cell; and
(c) a step for comparing this effector activity with the effector activity when the said test substance has been brought into contact with a control cell having no recombinant vector containing a DNA encoding an inventive protein but having a recombinant vector containing a DNA encoding a GPCR, whereby selecting a test substance causing a difference in the effector activity between the test cell and the control cell.

In the second method, a test substance which gives the effector activity of a test cell having an inventive protein expression vector which is higher than the effector activity in a control cell having no such a vector may be searched for. As a result, a substance which activates any stage of the signal transduction mediated by a GPCR and the inventive protein can be selected as a candidate compound.

A test substance which increase the effector activity of a test cell for example by about 20%, preferably about 50%, more preferably about 100%, when compared with a control cell can be selected as a signal transduction activator.

Otherwise, the aspect is similar to that in of the first method discussed above.

<Third Method>

A method for screening for a substance capable of regulating a signal transduction mediated by a GPCR and an inventive protein comprising:
(a) a step for bringing a test substance into contact with a test cell having a recombinant vector containing an inventive polynucleotide (which herein is a DNA encoding an inventive protein) and a recombinant vector containing a DNA encoding a GPCR;
(b) a step for measuring the G protein effector activity in the test cell; and
(c) a step for comparing this effector activity with the effector activity when the said test substance has been brought into contact with a control cell having no recombinant vector containing a DNA encoding a GPCR but having a recombinant vector having a DNA encoding an inventive protein, whereby selecting a test substance causing a difference in the effector activity between the test cell and the control cell.

In the third method, a test substance which gives the effector activity of a test cell having a GPCR expression vector which is higher than the effector activity in a control cell having no GPCR expression vector may be searched for. As a result, a GPCR agonist can be selected as a candidate substance.

A test substance which increase the effector activity of a test cell for example by about 20%, preferably about 50%, more preferably about 100%, when compared with a control cell can be selected as a signal transduction activator.

Otherwise, the aspect is similar to that in of the first method discussed above.

<Fourth Method>

A method for screening for a substance capable of regulating a signal transduction mediated by a GPCR and an inventive protein comprising:
(a) a step for bringing a test substance and a GPCR ligand into contact with a test cell having a recombinant vector containing an inventive polynucleotide (which herein is a DNA encoding an inventive protein) and a recombinant vector containing a DNA encoding a GPCR protein;
(b) a step for measuring the G protein effector activity in the test cell; and
(c) a step for comparing this effector activity with the effector activity in the test cell which has not been brought into contact with the test substance but has been brought into contact with the ligand, whereby selecting a test substance capable of altering the effector activity in the test cell.

In the fourth method, a test substance which gives increased or reduced effector activity in the control cell which has not been brought into contact with the test substances when compared with the effector activity in the test cell which has been brought into contact with the test substances may be searched for. As a result, a substance which activates or inhibits any stage of the signal transduction initiated from the binding of a GPCR ligand to a GPCR can be selected, including a GPCR agonist or antagonist.

A GPCR ligand may for example be amine molecules. It is preferable especially to use dopamine. The ratio between a ligand to be brought into contact with a cell and a test substance, when represented as the molar ratio of ligand:test substance, may for example be about 1:0.1 to 1:100, preferably about 1:1 to 1:50.

The percentage effector activity in a test cell which has been brought into contact with the both of a GPCR ligand and a test substance is calculated, on the bases of the effector activity in the test cell which has been brought into contact only with the GPCR ligand being regarded as 100% and the effector activity in the test cell which has been brought into contact with none of the GPCR ligand or the test substance as 0%. A test substance which gives a % effector activity in a test cell which has been brought into contact with the both of a GPCR ligand and the test substance of 85% or less, preferably 70% or less, especially 50% or less can be selected as a candidate of the cellular signal transduction inhibitor or suppressor. On the other hand, a test substance which raises this percentage to 125% or more, preferably 150% or more, especially 200% or more can be selected as a candidate of the cellular signal transduction activator.

Otherwise, the aspect is similar to that in of the first method discussed above.

<Fifth Method>

A method for screening for a substance capable of regulating a signal transduction mediated by a GPCR and an inventive protein comprising:
(a) a step for bringing a test substance and a GPCR ligand into contact with a test cell having a recombinant vector containing an inventive polynucleotide (which herein is a DNA encoding an inventive protein) and a recombinant vector containing a DNA encoding a GPCR protein;
(b) a step for measuring the G protein effector activity in the test cell;
(c) a step for comparing this effector activity with the effector activity in the test cell which has not been brought into contact with the test substance but has been brought into contact with the ligand, whereby investigating the change in the effector activity in the test cell; and
(d) a step for comparing the rate of change in this effector activity with the rate of change in the effector activity when the said test substance and said ligand has been brought into contact with a control cell having no recombinant vector containing a DNA encoding a GPCR but having a recombinant vector containing a DNA encoding an inventive protein, whereby selecting a test substance causing a difference in the rate of change in the effector activity between the test cell and the control cell.

In the fifth method, a test substance which gives an elevated rate of change in the effector activity in a test cell having a recombinant vector containing a DNA encoding a GPCR protein when compared with the rate of change in the effector activity in a control cell having no such a vector may be searched for. As a result, a substance which serves as an antagonist against an exogenous GPCR can be selected. While in the fourth method described above an antagonist against an endogenous GPCR is also selected, by subjecting the substances obtained by the fourth method to a screening by the fifth method, a substance serving as an antagonist against the endogenous GPCR can selectively be eliminated.

A test substance which increase the rate of change in the effector activity of a test cell for example by about 15%, preferably about 30%, more preferably about 50%, when compared with a control cell can be selected as a candidate of an exogenous GPCR-directed antagonist.

Otherwise, the aspect is similar to that in of the first method discussed above.

<Sixth Method>

A method for screening for a substance capable of regulating a signal transduction mediated by a GPCR and an inventive protein comprising:
(a) a step for bringing a test substance into contact with a cell membrane fraction of a cell having a recombinant vector containing an inventive polynucleotide (which herein is a DNA encoding an inventive protein) and a cell membrane fraction of a cell having a recombinant vector containing a DNA encoding a GPCR, or
a cell membrane fraction of a cell having the recombinant vector containing a polynucleotide encoding an inventive protein (which herein is a DNA encoding an inventive protein) and the recombinant vector containing the DNA encoding the GPCR;
(b) a step for assaying the level of the binding of GTP to the cell membrane fraction; and
(c) a step for comparing the assayed level of this GTP binding with the assayed level of the GTP binding to the cell membrane fraction which has not been brought into contact with the test substance, whereby selecting a test substance capable of altering the assayed level of the GTP binding to the cell membrane fraction.

When a cell expressing a GPCR and a G protein is stimulated by a GPCR ligand, then a GTP is bound to a G protein α subunit. This phenomenon is observed also in a membrane fraction of a cell which expresses a GPCR and a G protein. Accordingly, in the sixth method, a substance which increases the level of the binding of a GTP to this cell membrane fraction can be selected as a GPCR agonist.

Usually, a GTP bound to a G protein α subunit is decomposed into a GDP. Accordingly, a GTP analogue which is capable of binding to an inventive protein but is not decomposed by a GTPase is used to measure the level of the binding of this GTP analogue to an inventive protein, whereby assaying the level of the binding of the GTP to the inventive protein. Such a GTP analogue may for example be a GTPγS, $G_{pp}NH_p$ and the like.

For measuring the level of the binding of a GTP analogue to a cell membrane fraction, the GTP analogue is labeled for example with a radiolabel, and then the labeled GTP analogue is added to the cell membrane fraction and incubated for a certain period, and then the radioactivity in the cell membrane fraction is measured by a scintillation counter and the like.

The methods for preparing and characterizing a cell membrane fraction are as described above.

A test substance which increases a level of the binding of a GTP to a cell membrane fraction in a test cell which has been brought into contact with a test substance for example by about 25%, preferably about 50%, more preferably about 100%, when compared with a test cell which has not been brought into contact with a test substance can be selected as a candidate GPCR agonist.

Otherwise, the aspect is similar to that in of the first method discussed above.

<Seventh Method>

A method for screening for a substance capable of regulating a signal transduction mediated by a GPCR and an inventive protein comprising:
(a) a step for bringing a test substance and a GPCR ligand into contact with
a cell membrane fraction of a cell having a recombinant vector containing an inventive polynucleotide (which herein is a DNA encoding an inventive protein) and a cell membrane fraction of a cell having a recombinant vector containing a DNA encoding a GPCR, or
a cell membrane fraction of a cell having the recombinant vector containing a polynucleotide encoding an inventive protein (which herein is a DNA encoding an inventive protein) and the recombinant vector containing the DNA encoding the GPCR;
(b) a step for assaying the level of the binding of GTP to this cell membrane fraction; and
(c) a step for comparing the assayed level of this GTP binding with the assayed level of the GTP binding in the cell membrane fraction which has not been brought into contact with the test substance but has been brought into contact with said ligand, whereby selecting a test substance capable of altering the assayed level of the GTP binding to the cell membrane fraction.

In the seventh method, a substance which activates or inhibits (or suppresses) any stage (through the time of the binding of a GTP to a G protein α subunit) in a cellular signal transduction can be searched for, including GPCR receptor agonist and antagonist.

The percentage radioactivity in a membrane fraction which has been brought into contact with the both of a GPCR ligand and a test substance is calculated, on the bases of the radioactivity in the membrane fraction which has been brought into contact only with the GPCR ligand being regarded as 100% and the radioactivity in the membrane fraction which has been brought into contact with none of the GPCR ligand or the test substance as 0%. A test substance which gives a % radioactivity when brought into contact with the both of a GPCR ligand and the test substance of 75% or less, preferably 50% or less, especially 25% or less can be selected as a candidate of the cellular signal transduction inhibitor or suppressor. On the other hand, a test substance which raises the percentage radioactivity when brought into contact with the both of a GPCR ligand and the test substance to 125% or more, preferably 150% or more, especially 200% or more can be selected as a candidate of the cellular signal transduction activator.

Otherwise, the aspect is similar to that in of the sixth method discussed above. A ligand which can be employed and the ratio between the ligand and a test substance are similar to those in the fourth method.

<Eighth Method>

A method for screening for a substance capable of regulating a signal transduction mediated by a GPCR and an inventive protein comprising:
(a) a step for bringing a test substance into contact with a test cell capable of expressing a protein of the invention;

(b) a step for measuring the expression level of the protein of the invention in the test cell; and (c) a step for comparing this expression level with the expression level of said protein in the test cell which has not been brought into contact with the test substance, whereby selecting a test substance capable of altering the expression level of said protein in the test cell.

In this method, a substance which activates or inhibits a signal transduction mediated by an inventive protein by increasing or reducing the expression of the inventive protein can be selected.

The expression level of an inventive protein can be determined by measuring the level of the corresponding mRNA. The level of this mRNA can be determined by a known method such as a Northern blotting using an inventive probe described above or a PCR using inventive primers described above.

Specifically, a Northern blotting can be conducted in such a manner that an RNA is prepared from a test cell by a standard method, transferred onto a nylon membrane and the like, hybridized with a probe labeled for example with a radioisotope or fluorescent substance, and then a double strand of the probe with the RNA is detected by a method suitable for the label. A PCR can be conducted in such a manner that a cDNA is prepared from a mRNA of a test cell and used as a template to perform a PCR by a standard method using an inventive oligonucleotide set as primers.

The expression level of an inventive protein can be determined by quantifying the protein directly. The level of this protein can be determined by a known method such as a Western blotting using an inventive antibody.

As a cell expressing an inventive protein, a mammalian cell, preferably a human cell is employed. It is preferred particularly to use a cell derived from a human brain, thymus, testes, spleen, small intestine, uterus and heart.

<Inventive Screening Kit>

A first inventive kit for screening for a substance capable of regulating a signal transduction mediated by a GPCR and a protein according to the invention comprises a test cell having a recombinant vector containing an inventive polynucleotide (which herein is a DNA) and a reagent for measuring the G protein effector activity.

This kit can be used in the first inventive screening method described above. A test cell and the reagents for measuring a C protein effector activity are as described above. For performing the first screening method using this kit, the test cell is transduced with a recombinant vector having a DNA encoding a GPCR independently. Alternatively, the test cell may be one having a GPCR expression vector in addition to a recombinant vector having an inventive polynucleotide.

Furthermore, the first inventive screening kit may contain a control cell which does not have a recombinant vector having an inventive polynucleotide (which herein is a DNA) but has a control cell having a recombinant vector having a DNA encoding a GPCR. In such a case, it can be used in the second inventive screening method.

Moreover, the first inventive screening kit may contain a control cell which does not have a recombinant vector having a DNA encoding a GPCR but has an inventive polynucleotide (which herein is a DNA). In such a case, it can be used in the third inventive screening method.

The first inventive screening kit may further contain a GPCR ligand. In such a case, it can be used in the fourth inventive screening method. A ligand is employed also as described above.

The first inventive screening kit may further contain a GPCR ligand and a control cell having no recombinant vector having a DNA encoding a GPCR but having a recombinant vector having an inventive polynucleotide (which herein is a DNA). In such a case, it can be used in the fifth inventive screening method.

The second inventive kit for screening for a substance capable of regulating a signal transduction mediated by a GPCR and a protein according to the invention comprises a cell having a recombinant vector containing an inventive polynucleotide (which herein is a DNA); and a GTP analogue which can bind to the protein of the invention but can not be cleaved by a GTPase. This kit can be employed in the sixth inventive screening method. A GTP analogue is employed also as described above.

For performing the sixth screening method using this kit, a cell is transduced with a recombinant vector having a DNA encoding a GPCR independently. Alternatively, such a cell may be one having a GPCR expression vector in addition to a recombinant vector having an inventive DNA.

The third inventive kit for screening for a substance capable of regulating a signal transduction mediated by a GPCR and a protein according to the invention comprises a cell having a recombinant vector containing an inventive polynucleotide (which herein is a DNA) and a GPCR expression vector; and a GTP analogue which can bind to the protein of the invention but can not be cleaved by a GTPase. This kit can be employed in the sixth inventive screening method.

Each of the second and third screening kits according to the invention may further contain a GPCR ligand. In such a case, it can used in the 7th inventive screening method.

The fourth inventive kit for screening for a substance capable of regulating a signal transduction mediated by a GPCR and a protein according to the invention comprises a cell capable of expressing a protein of the invention; as well as an inventive probe, inventive primers or inventive antibody. This kit can be used in the 8th inventive screening method.

<Pharmaceuticals>

A protein and an antibody according to the invention can be used as pharmaceuticals by being administered in an effective amount to a mammal such as a human in the forms described below.

A protein and an antibody according to the invention can be formulated into pharmaceutical composition in a mixture with inactive carriers, such as pharmaceutically acceptable carriers (including excipient, extender, binder, lubricant and the like) as well as customary additives. Such a pharmaceutical composition may be given orally or parenterally depending on the dosage form (oral formulation such as tablet, pill, capsule, powder, granule, syrup and the like; parenteral formulation such as injection formulation, drip infusion formulation, dermal formulation, suppository and the like). The dose may vary depending on the type of the active ingredient, administration route, subject and the age, body weight and conditions of the patient, and may be about 0.01 to 100 mg a day, which can be given all at once or in several portions.

A polynucleotide, antisense polynucleotide and ribozyme of the invention can be administered in an effective amount to a mammal such as a human as pharmaceuticals in the forms of the pharmaceutical compositions described above. Otherwise, they can be introduced into a cell of a subject utilizing a liposome delivery system employing a liposome in which a drug to be delivered is encapsulated, a microinjection method, a direct injection method, an gene gun and the like. Also in such cases, the dose and the administration mode can be selected appropriately by those skilled in the art, although it may vary depending on the age, body weight and conditions of the patient.

An inventive polynucleotide can be introduced into a target cell also by integrating into a virus vector for a gene therapy.

A substance capable of regulating a signal transduction obtained by an inventive screening method can be administered in an effective amount to a mammal such as a human in the forms of the pharmaceutical compositions described above. When this substance is one encoded by a DNA, it can be introduced into a target cell also by integrating into a virus vector for a gene therapy.

EFFECT OF THE INVENTION

According to the invention, a protein which can be regarded as a novel G protein involved in a cellular signal transduction and a polynucleotide encoding the same are provided.

Moreover, an inventive protein can be regarded as a protein involved in a signal transduction mediated by a GPCR and a G protein involved in the differentiation and the proliferation of a cell, since the G protein effector activity in a cell having vectors expressing the GPCR and the inventive protein respectively is higher than the relevant effector activity in a cell having no vector expressing the inventive protein.

Furthermore, an inventive protein is considered to be one of G proteins, since it has regions having a high homology with the amino acid sequence conserved as a GTP binding site and a GTPase activation site among G proteins and the amino acid sequence of a trimer forming domain conserved among G proteins.

Accordingly, an inventive protein and a polynucleotide encoding the same can preferably be employed as a regulator of an intracellular signal transduction mediated by a GPCR and the inventive protein. Moreover, it is useful in treating or preventing a disease caused by the abnormality in this cellular signal transduction. Specifically, it can preferably be employed for treating or preventing a disease caused by an intracellular signal transduction due to the defect, reduced expression level or reduced function of a protein of the invention.

Moreover, an inventive polynucleotide can preferably used in the screening for a substance capable of regulating a signal transduction mediated by a GPCR stimulation.

Inventive antibody, antisense and ribozyme are employed preferably as regulators of an intracellular signal transduction mediated by a GPCR and an inventive protein. In addition, they can be used preferably in treating or preventing a disease caused by an abnormality in this intracellular signal transduction. They are useful preferably for the purpose especially of suppressing the increased abnormality in this intracellular signal transduction.

Furthermore, an antibody of the invention can preferably be used also in the affinity chromatography for purifying an inventive protein as well as in the screening for a substance which may affect the expression of an inventive protein.

A substance obtained by a screening method of the invention can be used as a regulator of a signal transduction mediated by a GPCR and an inventive protein. In addition, it can be used preferably in treating or preventing a disease caused by an abnormality in this intracellular signal transduction.

An inventive oligonucleotide can preferably be used in diagnosing of a disease caused by an intracellular signal transduction due to the defect of, and abnormally increased or reduced expression level of a protein of the invention.

Since an inventive protein is found to be expressed in the tissue of a brain such as a cerebrum, the inventive protein, polynucleotide, antibody, antisense, ribozyme and a substance obtained by an inventive screening method are considered to be useful in preventing or treating a neuropathy, and the like. An inventive oligonucleotide is also considered to be useful in diagnosing a neuropathy.

Also since an inventive protein is found to be expressed in a heart, the inventive protein, polynucleotide, antibody, antisense, ribozyme and a substance obtained by an inventive screening method are considered to be useful in preventing or treating a cardiac disease and the like (Targets, 2002, vol. 1, p 206-213).

Also since an inventive protein is found to be expressed in a thymus and a spleen, the inventive protein, polynucleotide, antibody, antisense, ribozyme and a substance obtained by an inventive screening method are considered to be useful in preventing or treating an immune disease and the like.

EXAMPLES

The present invention is further described in the following Examples, which are not intended to restrict the invention.

In the following Examples, an inventive protein is sometimes abbreviated as "Gm1".

Example 1

Cloning of cDNA Encoding Human Gm1 Protein

A pCR-Gm1 which is a plasmid comprising a DNA encoding a full-length human Gm1 was prepared as described below.

20 ng of a plasmid DNA from a human brain-derived cDNA library (Takara) (pAP3neo) was employed as a template together with 10 µM of a forward primer: prGm1ATG (5'-ATGGGTCTGTGCTACAGTCTGCGG; SEQ ID No:11) and 10 µM of a reverse primer prGNAL3' (5'-TCACAAGAGCTCATACTGCTT; SEQ ID No:12) as well as TAKARA LA Taq polymerase (TAKARA LA Taq with GC Buffer, Takara) to perform a PCR to obtain an amplified DNA.

The PCR condition involved 35 cycles, each cycle involving incubations at 95° C. for 30 seconds followed by 60° C. for 30 seconds followed by 72° C. for 2 minutes.

The resultant DNA was subjected to an agarose gel electrophoresis followed by a purification with a QIAquick Gel Extraction kit (QIAGEN), and then recovered. This purified and recovered DNA was used as an insert DNA.

Subsequently, a TOPO TA Cloning Kit (Invitorogen) was used and the attached protocol was followed to insert the insert DNA (50 ng) into a cloning site of a pCR2.1-TOPO vector (10 ng), whereby obtaining a pCR-Gm1.

The DNA thus obtained was subjected to an ABI377 DNA sequencer to determine the nucleotide sequence, and was revealed to contain the nucleotide sequence of the nucleotide Nos. 1-1377 in the nucleotide sequence represented by SEQ ID NO:2 and to encode the full-length amino acid sequence represented by SEQ ID NO:1.

Example 2

Detection of Expression Profile of Nucleic Acid Encoding Gm1

In order to amplify a nucleic acid encoding Gm1 specifically, a forward primer prGm1rt-5' (5'-ATGGGGT-GTTTGGGCGGCAACA; SEQ ID No:13) and a reverse primer prGm1rt-3' (5'-ACGATGGTGCTTTTCCCAGACT-CACCAGCCCCGAGCA; SEQ ID No:14) were produced. Each 1 µg of human bone marrow-derived total RNA (Ambion), human brain-derived total RNA (Ambion), human spreen-derived total RNA (Ambion), human thymus-derived total RNA (Ambion), human small intestine-derived total RNA (Ambion), human liver-derived total RNA (Ambion), human placenta-derived total RNA (Ambion), human cervix-derived total RNA (Ambion), human uterus-derived total RNA (Ambion), human heart-derived total RNA (Ambion), human skeletal muscle-derived total RNA (Ambion), human testis-derived total RNA (Ambion) and human kidney-derived total RNA (Ambion) were employed as templates together with each 10 µM of the primer set described above and a SuperScript One-Step RT-PCR System (Invitrogen) and the attached protocol was followed to conduct a RT-PCR to amplify a mRNA. The condition of the RT-PCR involved an incubation at 55° C. for 30 minutes for a reverse transcription reaction, followed by 35 cycles, each cycle involving incubations at 94° C. for 20 seconds followed by 60° C. for 30 seconds followed by 72° C. for 1 minute.

Then, 20 µl of the RT-PCR product was subjected to an agarose gel electrophoresis, stained with ethidium bromide, and irradiated with UV to identify the signals amplified specifically. The gel photograph is shown in FIG. 1. As evident from FIG. 1, Gm1 is expressed highly in brain, thymus, testis, spleen, small intestine, uterus and heart.

Example 3

In situ Hybridization in Brain Tissue (Detailed Analysis of Expression Profile of Nucleic Acid Encoding Inventive Protein in Brain Tissue)

The expression profile of a nucleic acid encoding the inventive protein in brain tissue was investigated by the following method.

For conducting an in situ hybridization in a mouse brain tissue, the following procedure was employed to clone a cDNA in the 5' terminal region of a mouse Gm1 gene.

20 ng of a mouse brain-derived cDNA (Clontech) was employed as a template together with 10 µM of a forward primer prmGm1-1 (5'-ATGGGCCTATGCTACAGCCT-GCGGCCGCT; SEQ ID No:15) and 10 µM of a reverse primer prmGm1-2 (5'-GCTGCAGGTCCCGCTTCT-GCTCGCGCAGCATGCGGT; SEQ ID No:16) as well as TAKARA LA Taq polymerase (TAKARA LA Taq with GC Buffer, Takara) to perform a PCR to obtain an amplified DNA.

The PCR condition involved 35 cycles, each cycle involving incubations at 95° C. for 30 seconds followed by 60° C. for 30 seconds followed by 72° C. for 2 minutes. The resultant DNA was subjected to an agarose gel electrophoresis followed by a purification with a QIAquick Gel Extraction kit (QIAGEN), and then recovered. This purified and recovered DNA was used as an insert DNA.

Then, a QIAGEN PCR Cloning kit (QIAGEN) was used following to its attached protocol to insert the insert DNA (50 ng) into a cloning site of a pDrive vector (10 ng), whereby producing a pDrmGm1.

Similarly, a QIAGEN PCR Cloning kit (QIAGEN) was used following to its attached protocol to insert the insert DNA (50 ng) to a cloning site of a pDrive vector (10 ng), whereby obtaining a pDrmGolf.

(Production of Probe for in situ Hybridization)

1 µg of a pDrmGm1 plasmid was cleaved with a restriction enzyme HindIII or BamHI to obtain a linear plasmid pDrmGm1/HindIII and pDrmGm1/BamHI$_o$ L µg of a pDrmGm1/HindIII, 2 µl of a DIGRNALabelingMix (Roche, Diagnostic) and 1 µl of a SP6RNA polymerase (Roche, Diagnostic) were mixed and incubated at 37° C. for 3 hours in the presence of the attached buffer. Then, 1 µl of a DNaseI (Roche, Diagnostic) was added and the mixture was incubated at 37° C. for 30 minutes to obtain a cRNA. This cRNA was precipitated with ethanol, suspended in 20 µl of a TE buffer, and used as an mGm1 sense cRNA.

Similarly, 1 µg of a pDrmGm1/BamHI, 2 µl of a DIGR-NALabelingMix (Roche, Diagnostic) and 1 µl of SP6RNA polymerase (Roche, Diagnostic) were mixed, and incubated at 37° C. for 3 hours in the presence of the attached buffer. Then, 1 µl of a DnaseI (Roche, Diagnostic) was added and incubated at 37° C. for 30 minutes to obtain a cRNA. This cRNA was precipitated with ethanol, suspended in a 20 µl of TE buffer, and used as an mGm1 antisense cRNA.

(Detection by in situ Hybridization)

A detailed analysis of the expression profile of mRNA of the Gm1 in a brain is conducted by an in situ hybridization using a labeled cRNA [Simmons et al., J. Histotechnol. 12:169-181 (1989)]. Thus, from a mouse brain fixed using paraformaldehyde and glutaraldehyde by a known method, a brain section whose thickness is 50 µm is prepared using a brain section producing device (sliding microtome), and then adsorbed on a glass slide and dried. The brain section is made free from the paraffin, autoclaved in a target solution (Daco) (105° C., 10 minutes), dehydrated, and dried in the air. The hybridization with a probe (100 ng cRNA) is conducted in a hybridization buffer (40% formamide, 4×SSC, 1 mMEDTA, 250 µg/ml yeast tRNA, 1× Denhardt's solution, 10% dextran sulfate) at 60° C. overnight. Thereafter, the brain section is washed at 65° C. with 2×SSC, 0.1% SDS solution, treated with an RNaseA (10 µg/ml, 37° C., 30 minutes), washed with 2×SSC, 50% formamide solution, dehydrated, dried in the air, and subjected to a mRNA detection using a DlG labeled antibody detection kit (Daco).

Example 4

Construction of Expression Plasmid for Expression of Human Gm1 Protein in *E. Coli*

In order to express a large amount of a human Gm1 protein in *E.coli*, a human Gm1 protein is first expressed as a fusion protein with a glutathion S transferase, and then only the part of the human Gm1 protein is cut out from the fusion protein.

Thus, the human Gm1 cDNA fragment-containing plasmid pCR-Gm1 obtained in Example 1 is double-digested with EcoRV and SpeI, and imparted with a blunt end with a Blunting Kit (Takara). The resultant DNA is subjected to an agarose gel electrophoresis and then purified using a QIAquick Gel Extraction Kit (QIAGEN) and then recovered. The recovered DNA is used as an insert DNA. The pGEX-5X-1 which had been cleaved with EcoRV and then BAP-treated is employed as a vector, and 50 ng of this vector and 10 ng of the insert DNA are ligated using a T4 ligase, whereby producing an expression plasmid pGEX-Gm1.

Example 5

Purification of Recombinant Human Gm1 Protein from *E. Coli* Expressing Glutathion S Transferase-Human Gm1 Fusion Protein The glutathion S transferase-human Gm1 fusion protein-expressing plasmid pGEX-Gm1 obtained in Example 4 is used to transform an *E.coli* (*Escherichia coli*) JM109 strain by a calcium method. The resultant transformant is cultured in a 50 µg/ml ampicillin (Sigma)-supplemented LB medium at 37° C., and, once the O.D.$_{600}$ becomes about 0.6 reached, 1 mM (final concentration) of isopropyl-β-D-thiogalactopyranoside (IPTG) is added to induce the protein expression, and incubated for further 6 hours, prior to the recovery of the cells.

The cells are disrupted with ultrasonic treatment, centrifuged at 10,000 g for 5 minutes to obtain a soluble fraction. The resultant soluble fraction is applied onto an anti-glutathion S transferase monoclonal antibody column (Amersham Bioscience) to purify a glutathion S transferase-human Gm1 fusion protein. Then, the purified glutathion S transferase-human Gm1 fusion protein is treated with an active blood coagulation factor X (New England Biolabo) to cut a human Gm1 protein out.

The human Gm1 protein thus cut out is subjected sequentially to a cation exchange column (S-sepharose FF; Pharmacia), hydrophobic column (Phenyl-superose; Pharmacia), hydroxyapatite column (MITSUI TOATSU CHEMICALS), cation exchange column (MONOS; Pharmacia) to purify the human Gm1 protein until it shows an almost single band in an SDS-PAGE analysis with Coomassie brilliant blue staining.

Example 6

Production of Human Gm1 Protein Partial Peptide and Production of Anti-Human Gm1 Peptide Antibody Using this Peptide An antibody specific to a human Gm1 protein was prepared by the procedure shown below. A peptide consisting of 14 amino acids of the amino acid Nos. 7 to 20 in the amino acid sequence represented by SEQ ID No:1 was synthesized.

This peptide was bound to a carrier protein KML and used as an immunogen. The resultant KML fusion peptide ptGm1 was used to immunize a New Zealand white rabbit to produce an anti-human Gm1 peptide serum. The immunization was repeated 5 times. From this rabbit, an antiserum was collected, and the antiserum was purified using a protein G column (Amersham Bioscience) to isolate an antigen-specific anti-human Gm1 protein antibody.

Example 7

Construction of Expression Vector for Expression of Human Gm1 Protein in Animal Cell An expression vector for transient expression of a human Gm1 protein in an animal cell is constructed. Thus, first, the human Gm1 cDNA fragment-containing pCR-Gm1 obtained in Example 1 is double-digested with restriction enzymes XbaI and KpnI, and the resultant DNA fragment is introduced into a pcDNA3.1 at XbaI site and KpnI site whereby obtaining an expression vector pcDNA-Gm1 for a transient expression of human Gm1 protein in an animal cell.

Example 8

Construction of Expression Vectors for Expression of Human Dopamine Receptor Proteins in Animal Cell Expression vectors for transient expression in an animal cell of a human dopamine D1 receptor protein and a human dopamine D2 receptor protein respectively were constructed by the following procedure.

In order to amplify a DNA encoding a human dopamine D1 receptor, 20 ng of a plasmid DNA from a human brain-derived cDNA library (Takara) (pAP3neo) was employed as a template together with 10 µM of a forward primer prDopaminD1-5' (5'-agctcggatccATGAGGACTCTGAACACCTCTGCCA; (SEQ ID NO:17) and 10 µM of a reverse primer prDopaminD1-3' (5'-gtgcagaattcTCATCTGCGAGTTCAGGTTGGGT; SEQ ID No:18) as well as a TAKARA LA Taq polymerase (TAKARA LA Taq with GC Buffer, Takara) to perform a PCR.

In order to amplify a DNA encoding a human dopamine D2 receptor, 20 ng of a plasmid DNA from a human brain-derived cDNA library (Takara) (pAP3neo) was used as a template together with 10 µM of a forward primer prDopaminD2-5' (5'-agctcggatccATGGATCCACTGAATCTGTCCTGGTATGA; SEQ ID No:19) and 10 µM of a reverse primer prDopaminD2-3' (5'-gtgcagaattcTCAGCAGTGAAGGATCTTCTGGAAGGCCTT; SEQ ID No:20) as well as a TAKARA LA Taq polymerase (TAKARA LA Taq with GC Buffer, Takara) to perform a PCR.

The PCR condition involved 35 cycles, each cycle involving incubations at 95° C. for 30 seconds followed by 60° C. for 30 seconds followed by 72° C. for 2 minutes. The resultant DNA was subjected to an agarose gel electrophoresis followed by a purification with a QIAquick Gel Extraction kit (QIAGEN), and then recovered. This purified and recovered DNA was used as an insert DNA.

Each insert DNA was double-digested with BamHI and EcoRI, introduced into a pcDNA3.1(+) at BamHI and EcoRI sites, whereby obtaining animal cell expression vectors pcDNA-D1R and pcDNA-D2R.

Example 9

Construction of Baculovirus Vector Encoding Human Gm1 Protein

First, a transfer vector for overexpressing a human Gm1 protein in an insect cell was constructed. The human Gm1 cDNA fragment-containing pCR-Gm1 obtained in Example 1 was double-digested with restriction enzyme XbaI and SpeI, and the resultant DNA fragment was introduced into a pAcMP2 (Pharmingen) at XbaI site to obtain a transfer vector pAcMP-Gm1. Then 5 µg of this transfer vector and 1 µg of a Baculovirus DNA, BaculoGold DNA (Pharmingen) were cotransfected to 2×10$^6$ cells of Sf21, which were cultured at 27° C. for 5 days, and then the culture supernatant was recovered to obtain a virus solution.

Example 10

Construction of Baculovirus Vector Encoding Human Gβ Protein

A transfer vector for overexpressing a human Gβ protein in an insect cell was constructed by the procedure described below.

In order to amplify a DNA encoding human Gβ protein, 20 ng of a plasmid DNA from a human brain-derived cDNA library (Takara) (pAP3neo) was employed as a template together with 10 μM of a forward primer prGb1-5' (5'-ATGAGTGAGCTTGACCAGTTACGGCA; SEQ ID No:21), 10 μM of a reverse primer prGb1-3' (5'-TTAGTTC-CAGATCTTGAGGAAGCTAT; SEQ ID No:22) as well as a TAKARA LA Taq polymerase (TAKARA LA Taq with GC Buffer, Takara) to perform a PCR. The PCR condition involved 35 cycles, each cycle involving incubations at 95° C. for 30 seconds followed by 60° C. for 30 seconds followed by 72° C. for 2 minutes. The resultant DNA was subjected to an agarose gel electrophoresis followed by a purification with a QIAquick Gel Extraction kit (QIAGEN), and then recovered. This purified and recovered DNA was used as an insert DNA. Then, a TOPO TA Cloning Kit (Invitorogen) was used in accordance with its attached protocol to insert the resultant insert DNA (50 ng) into a pCR2.1-TOPO vector (10 ng) at a cloning site whereby obtaining a pCR-Gβ.

Then, the pCR-Gβ was double-digested with restriction enzyme BamHI and NotI, and the resultant DNA fragment was introduced into a pAcMP3 (Pharmingen) at BamHI and NotI sites, whereby obtaining a transfer vector animal cell expression vector pAcMP-Gβ.

Then, 5 μg of this transfer vector and 1 μg of a Baculovirus DNA, BaculoGold DNA (Pharmingen) were cotransfected to $2\times10^6$ cells of Sf21 cell, which are cultured at 27 μ for 5 days, and then the culture supernatant was recovered to obtain a virus solution.

Example 11

Construction of Baculovirus Vector Encoding Human Gγ Protein

A transfer vector for overexpressing a human Gγ protein in an animal cell was constructed by the procedure described below.

In order to amplify a DNA encoding human Gγ protein, 20 ng of a plasmid DNA from a human brain-derived cDNA library (Takara) (pAP3neo) was employed as a template together with 10 μM of a forward primer prGg3-5' (5'-ATGAAAGGTGAGACCCCGGTGAACA; SEQ ID No:23), 10 μM a reverse primer prGg3-3' (5'-TCAGAG-GAGAGCACAGAAGAACTT; SEQ ID No:24) as well as a TAKARA LA Taq polymerase (TAKARA LA Taq with GC Buffer, Takara) to perform a PCR. The PCR condition involved 35 cycles, each cycle involving incubations at 95° C. for 30 seconds followed by 60° C. for 30 seconds followed by 72° C. for 2 minutes. The resultant DNA was subjected to an agarose gel electrophoresis followed by a purification with a QIAquick Gel Extraction kit (QIAGEN), and then recovered. This purified and recovered DNA was used as an insert DNA. Then, a TOPQ TA Cloning Kit (Invitorogen) was used in accordance with its attached protocol to insert each resultant insert DNA (50 ng) into a pCR2.1-TOPO vector (10 ng) at a cloning site whereby obtaining a pCR-Gγ.

Then, the pCR-Gγ was double-digested with restriction enzyme XbaI and PstI, and the resultant DNA fragment was introduced into a pAcMP3 (Pharmingen) at XbaI and PstI sites, whereby obtaining a transfer vector pAcMP-Gγ. Then, 5 μg of this transfer vector and 1 μg of a Baculovirus DNA, BaculoGold DNA (Pharmingen) were cotransfected to $2\times10^6$ cells of Sf21 cell, which are cultured at 27° C. for 5 days, and then the culture supernatant was recovered to obtain a virus solution.

Example 12

Construction of Baculovirus Vectors Encoding Human Dopamine D1 Receptor and Human Dopamine D2 Receptor Transfer vectors for overexpressing a human dopamine D1 receptor protein and a human dopamine D2 receptor protein respectively in an insect cell were constructed by the procedure described below.

The human dopamine D1 receptor expression vector pcDNA-D1R and the human dopamine D2 receptor expression vector pcDNA-D2R obtained in Example 8 were each double-digested with BamHI and EcoRI, and the resultant DNA fragments are each introduced into a pAcMP3 at BamHI and EcoRI sites, whereby obtaining transfer vectors pAcMP-D1R and pAcMP-D2R.

Then, each 5 μg of the either transfer vectors and 1 μg of a Baculovirus DNA, BaculoGold DNA (Pharmingen) were cotransfected to $2\times10^6$ cells of Sf21 cell, which are cultured at 27 μ for 5 days, and then the culture supernatants were recovered to obtain virus solutions.

Example 13

High Expression of Human Gm1 Protein Using Baculovirus Vector and Purification of the Protein A virus solution containing human Gm1 protein expression Baculovirus obtained in Example 9 was infected at MOI5 to $2\times10^7$ cells of SF21 cell, which were cultured at 27° C. Five days after the infection, the cells were recovered and suspended in an HE/PI buffer (20 mM HEPSE, 2 mM EDTA supplemented with 1× protenase inhibitor cocktail (NACALAITESQUE). The cell suspension was passed through a 26 G needle 15 times to disrupt the cell membrane. The suspension was then centrifuged at 4° C. and 100×g for 5 minutes, and the supernatant obtained was centrifuged at 4° C. and 20,000×g for 30 minutes, whereby recovering a human Gm1 protein-containing cell membrane fraction.

Example 14

High Expression of Human Gβ Protein and Human Gγ Protein Using Baculovirus Vector and Purification of the Proteins A virus solution containing human Gβ protein expression Baculovirus obtained in Example 10 and human Gγ protein expression Baculovirus obtained in Example 11 was infected at MOI5 to $2\times10^7$ cells of SF21 cell, which were cultured at 27° C. Five days after the infection, the cells were recovered and suspended in an HE/PI buffer (20 mM HEPSE, 2 mM EDTA supplemented with 1× Protenase inhibitor cocktail (NACALAITESQUE). The cell suspension was passed through a 26 G needle 15 times to disrupt the cell membrane. The cell suspension was then centrifuged at 4° C. and 110×g for 5 minutes, and the supernatant obtained was centrifuged at 4° C. and 20,000×g for 30 minutes, whereby recovering a cell membrane fraction containing the human Gβ protein and the human Gγ protein.

Example 15

High Expression of Human Dopamine D1 Receptor Protein and Human Dopamine D2 Receptor Gγ Protein Using Baculovirus Vector and Purification of the Proteins A virus solution containing either human dopamine D1 receptor protein expression Baculovirus or human dopamine D2 receptor protein expression Baculovirus obtained in Example 12 was infected at MOI5 to 2×10$^7$ cells of SF21 cell, which were cultured at 27° C. Five days after the infection, the cells were recovered and suspended in an HE/PI buffer (20 mM HEPSE, 2 mM EDTA supplemented with 1× Protenase inhibitor cocktail (NACALAITESQUE). The cell suspensions were passed through a 26 G needle 15 times to disrupt the cell membrane. This cell suspensions were then centrifuged at 4° C. and 110×g for 5 minutes, and the supernatants obtained were centrifuged at 4° C. and 20,000×g for 30 minutes, whereby recovering a cell membrane fraction containing the human dopamine D1 receptor protein or the human dopamine D2 receptor protein.

Example 16

GTP Binding Assay Using Human Gm1 Protein Expressed by Baculovirus Vector

The Gm1 protein-containing membrane fraction purified in Example 13 is employed to conduct a GTP binding assay.

The cell membrane fraction containing 2 µg of the Gm1 protein prepared in Example 13, the cell membrane fraction containing 2 µg of the Gβ protein and the Gγ protein prepared in Example 14 and the cell membrane fraction containing 2 µg of the dopamine D1 receptor protein prepared in Example 15 are suspended in 55 µl of a binding buffer (59 mM Tris, 4.8 mM MgCl$_2$, 2 mM EDTA, 100 mM NaCl, 1 µM GDP). One µM of dopamine is added and the mixture is incubated at 30° C. for 10 minutes. Thereafter, 200 µM of [35S]GTPγS is added and the mixture is incubated at 30° C. for 30 minutes.

Then 1.5 ml of a washing buffer (ice-cooled 50 mM Tris, 5 mM MgCl$_2$, 150 mM NaCl, 0.1% BSA, 0.05% CHAPS (pH7.4)) is added and the mixture is filtered through a glass fiber filter paper GF/F. Then this filter paper is washed three times with 1 ml of Tris (pH7.4), incubated at 65° C. for 30 minutes, subjected to a liquid scintillation counter to measure the radioactivity of the [35S]GTPγS which is bound to the membrane fraction depositing on the filter paper.

Example 17

Screening for Dopamine D1 Receptor Antagonist Using Change in cAMP Level as Index 2×10$^5$ Cells of CHO cell were transfected with 1 µg of the dopamine D1 receptor expression vector obtained in Example 8 and the Gm1 expression vector obtained in Example 7 (pcDNA-Gm1; 3 µg) by a lipofection method to prepare a test cell.

Then, the cells were inoculated to each well of a 96-well plate at 3×10$^4$ cells/well, and cultured for about 24 hours. Then, the culture medium was removed, and 80 µl of 1 mM IBMX-supplemented OPTI-MEN (Invitrogen) was added to the cells, which were then incubated at 37° C. for 10 minutes.

Then, 10 µM of dopamine as a GPCR ligand and 10 µM of each test substance (butaclamol, chlorpromazine, fluphenazine, haloperidol, SCH-23390) were added and incubated at 37° C. for 30 minutes.

Then, the reaction buffer was removed, and the cAMP level was determined using a HitHunter ECF cyclic AMP chemiluminescent assay kit (Applied Biosystems). As controls, a test cell which had been brought into contact only with the GPCR ligand at the same concentration and a test cell which had been brought into contact with nothing were examined for their cAMP levels in the similar manner.

Figure 2:
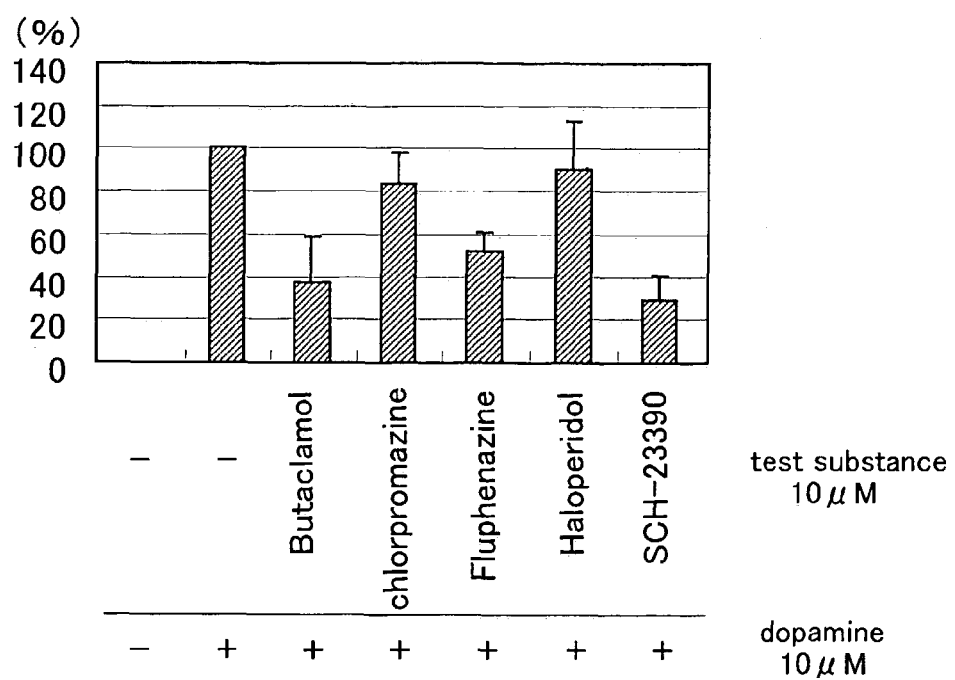
FIG. 2 is a schematic view indicating the dopamine D1 receptor antagonistic effects of various test substance (Example 17)

A substance which gave a cAMP level percentage of 85% or less upon contact with the ligand and the test substance was selected as a signal transduction inhibitor (antagonist), on the basis of the cAMP level with no contact being 0% and the cAMP level with the contact only with the ligand being 100% (FIG. 2).

Example 18

Screening of Dopamine D1 Receptor Using Change in cAMP Level as Index

2×10$^5$ Cells of CHO cell were transfected with the dopamine D1 receptor expression vector (1 µg) obtained in Example 8 and the Gm1 expression vector obtained in Example 7 (pcDNA-Gm1; 3 µg) by a lipofection method to prepare a test cell.

Then, the cells were inoculated to each well of a 96-well plate at 3×10$^4$ cells/well, and cultured for about 24 hours. Then, the culture medium was removed, and 80 µl of 1 mM IBMX-supplemented OPTI-MEN (Invitrogen) was added to the cells, which were then incubated at 37° C. for 10 minutes.

Then, 10 µM of dopamine as a GPCR ligand or 10 µM of a test substance (apomorphine, CY208-248, SKF-38393, SKF-81297) was added and incubated at 37° C. for 30 minutes.

Then, the reaction buffer was removed, and the cAMP level was determined using a HitHunter ECF cyclic AMP chemiluminescent assay kit (Applied Biosystems). As a control, a test cell which had been brought into contact with nothing were examined for their cAMP levels in the similar manner.

Figure 3:
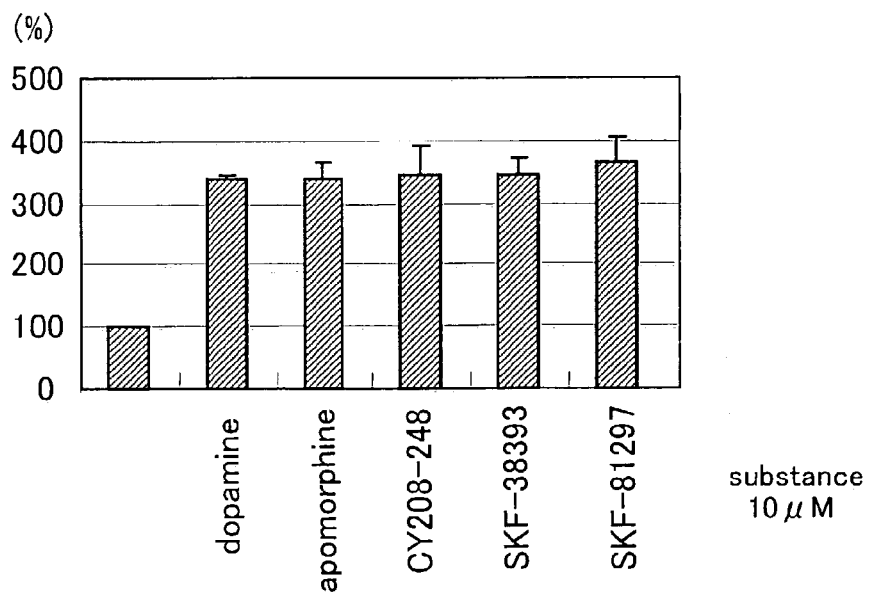
FIG. 3 is a schematic view indicating the dopamine D1 receptor agonistic effects of various test substance (Example 18)

A substance which gave a cAMP level percentage of 125% or more upon contact of the test cell with the test substance was selected as a signal transduction activator (agonist), on the basis of the cAMP level when the test cell has not been brought into contact with anything being 100% (FIG. 3).

Example 19

Screening Using Change in cAMP Level as Index

1×10$^6$ Cells of CHO cell are transfected with the dopamine D1 receptor expression vector obtained in Example 8 (100 ng), CRE-reporter plasmid (pCRE-1uc;20 ng; Stratagene) and the Gm1 expression vector obtained in Example 7 (pcDNA-Gm1; 30 ng) by a lipofection method to prepare a test cell.

Then the cells are inoculated to each well of a 24-well plate at 5×10$^3$ cells/well, and then cultured for about 48 hours. Then, the cells are washed with 0.2 mM buffer (3-isobutyl-methylxanthine, 0.05% BSA, 20 mM HEPES-supplemented Hunk's buffer (pH7.4); hereinafter referred to as "reaction buffer"). Then the reaction buffer is added to the cells, which are incubated at 37° C. for 30 minutes.

Then, the reaction buffer is removed, and 0.25 ml of a fresh reaction buffer is added to the cells, and then 1 nM dopamine as a GPCR ligand and 0.1 nM to 10 nM test substance are added and the mixture is incubated at 37° C. for 30 minutes. Then the cells are dissolved in a cell lysis solution (PICK-A-GENE luciferase kit, TOYO INK), and combined with a luminescent substrate (PICK-A-GENE luciferase kit, TOYO INK), and examined for the fluorescent intensity using a luminometer. As controls, a test cell which had been brought into contact only with the GPCR ligand at the same concentration and a test cell which had been brought into contact with nothing are examined for their fluorescent intensities in the similar manner.

A substance which gave a fluorescence intensity of percentage of 50% or less, or 150% or more upon contact with the ligand and the test substance is selected as a signal transduction regulating substance, on the basis of the fluorescent intensity with no contact being 0% and the fluorescent intensity with the contact only with the ligand being 100%.

Example 20

Construction of Expression Vector for Expression of Human Adenosine A2a Receptor Protein in Animal Cell An expression vector for transient expression of a human adenosine A2a receptor protein in an animal cell was constructed by the procedure described below.

In order to amplify a DNA encoding a human adenosine A2a receptor, 20 ng of a plasmid DNA from a human brain-derived cDNA library (Takara) (pAP3neo) was employed as a template together with 10 µM of a forward primer prAdenosineA2A-5' (5'-agctcggatccATGCCCAT-CATGGGCTCCTCGGTGTA; SEQ ID NO:33) and 10 µM of a reverse primer prAdenosineA2A-3' (5'-gtgcagaattcT-CAGGACACTCCTGCTCCATCCT; SEQ ID No:34) as well as a TAKARA LA Taq polymerase (TAKARA LA Taq with GC Buffer, Takara) to perform a PCR.

The PCR condition involved 35 cycles, each cycle involving incubations at 95° C. for 30 seconds followed by 60° C. for 30 seconds followed by 72° C. for 2 minutes. The resultant DNA was subjected to an agarose gel electrophoresis followed by a purification with a QIAquick Gel Extraction kit (QIAGEN), and then recovered. This purified and recovered DNA was used as an insert DNA.

Each insert DNA was double-digested with BamHI and EcoRI, introduced into a pcDNA3.1(+) at BamHI and EcoRI sites, whereby obtaining an animal cell expression vector pcDNA-A2a.

Example 21

Screening of Adenosine A2a Receptor Antagonist Using Change in cAMP Level as Index $2 \times 10^5$ Cells of CHO cell were transfected with the adenosine A2a receptor expression vector (1 µg) obtained in Example 20 and the Gm1 expression vector obtained in Example 7 (pcDNA-Gm1; 3 µg) by a lipofection method to prepare a test cell.

Then, the cells were inoculated to each well of a 96-well plate at $3 \times 10^4$ cells/well, and cultured for about 24 hours. Then, the culture medium was removed, and 80 µl of 1 mM IBMX-supplemented OPTI-MEN (Invitrogen) was added to the cells, which were then incubated at 37° C. for 10 minutes.

Then, 10 µM of adenosine as a GPCR ligand and 10 µM of a test substance (DMPX) were added and incubated at 37° C. for 30 minutes.

Then, the reaction buffer was removed, and the cAMP level was determined using a HitHunter ECF cyclic AMP chemiluminescent assay kit (Applied Biosystems). As controls, a test cell which had been brought into contact only with the GPCR ligand at the same concentration and a test cell which had been brought into contact with nothing were examined for their cAMP levels in the similar manner.

Figure 4:
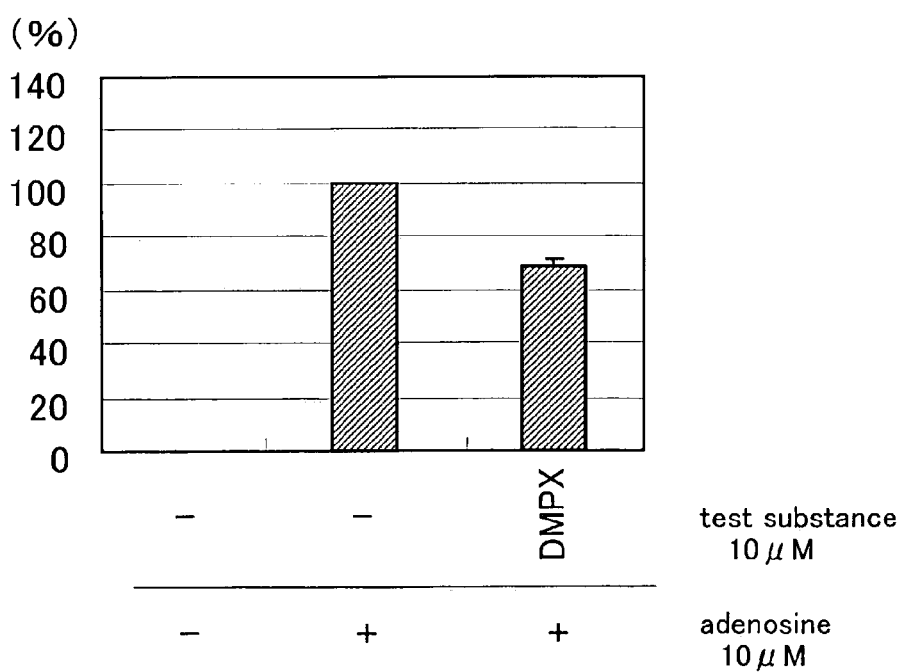
FIG. 4 is a schematic view indicating the adenosine A2a receptor antagonistic effects of DMPX (Example 21)

A substance which gave a cAMP level percentage of 85% or less upon contact of the cell with the ligand and the test substance was selected as a signal transduction inhibitor (antagonist), on the basis of the cAMP level with no contact being 0% and the cAMP level with the contact of the cell only with the ligand being 100% (FIG. 4).

Example 22

Screening of Adenosine A2a Receptor Agonist Using Change in cAMP Level as Index $2 \times 10^5$ Cells of CHO cell were transfected with the adenosine A2a receptor expression vector (1 µg) obtained in Example 20 and the Gm1 expression vector obtained in Example 7 (pcDNA-Gm1; 3 µg) by a lipofection method to prepare a test cell.

Then, the cells were inoculated to each well of a 96-well plate at $3 \times 10^4$ cells/well, and cultured for about 24 hours. Then, the culture medium was removed, and 80 µl of 1 mM IBMX-supplemented OPTI-MEN (Invitrogen) was added to the cells, which were then incubated at 37° C. for 10 minutes.

Then, 10 µM of adenosine as a GPCR ligand or 10 µM of a test substance (CGS-21680) was added and incubated at 37° C. for 30 minutes.

Then, the reaction buffer was removed, and the cAMP level was determined using a HitHunter ECF cyclic AMP chemiluminescent assay kit (Applied Biosystems). As a control, a test cell which had been brought into contact with nothing were examined for their cAMP levels in the similar manner.

Figure 5:
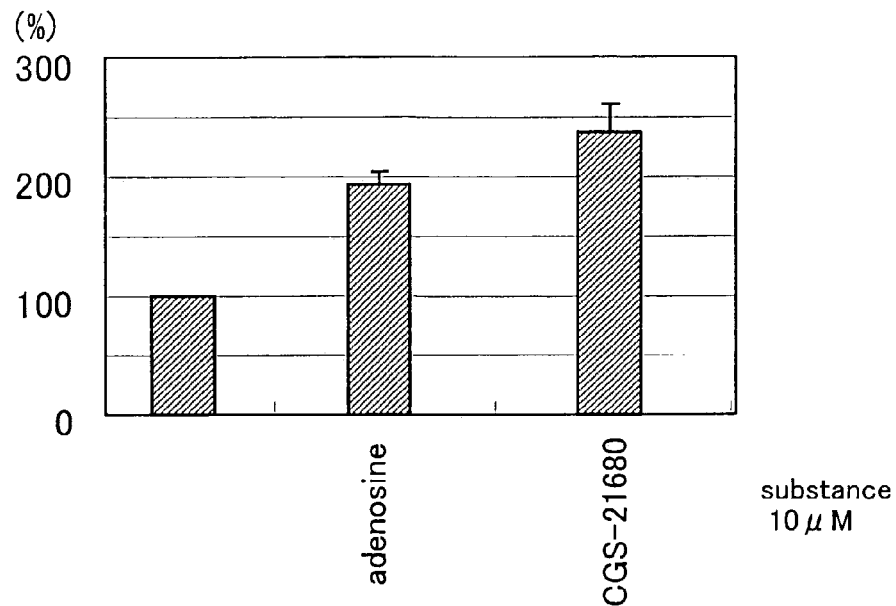
FIG. 5 is a schematic view indicating the adenosine A2a receptor agonistic effects of CGS-21680 (Example 22)

A substance which gave a cAMP level percentage of 125% or more upon contact with the test substance was selected as a signal transduction activator (agonist), on the basis of the cAMP level when the test cell has not been brought into contact with anything being 100% (FIG. 5).

Example 23

Screening by GTP Binding Assay

The cell membrane fraction containing 2 µg of the Gm1 protein prepared in Example 13, the cell membrane fraction containing 2 µg of the Gβ protein and Gγ protein prepared in Example 14 and the cell membrane fraction containing 2 µg of the dopamine D1 receptor protein prepared in Example 15 are suspended in 55 µl of a binding buffer (59 mM Tris, 4.8 mM MgCl$_2$, 2 mM EDTA, 100 mM NaCl, 1 µM GDP). 1 µM of dopamine and 0.1 nM-10 nM of a test substance (for example, 1 nM SCH-23390) are added and the mixture is incubated at 30° C. for 10 minutes. Thereafter, 200 pM of [35S]GTPγS is added and the mixture is incubated at 30° C. for 30 minutes.

Then 1.5 ml of a washing buffer (ice-cooled 50 mM Tris, 5 mM $MgCl_2$, 150 mM NaCl, 0.1% BSA, 0.05% CHAPS (pH7.4)) is added and the mixture is filtered through a glass fiber filter paper GF/F. Then this filter paper is washed three times with 1 ml of Tris (pH7.4), incubated at 65° C. for 30 minutes, subjected to a liquid scintillation counter to measure the radioactivity of the [35S]GTPγS which is bound to the membrane fraction depositing on the filter paper.

A substance whose radioactivity percentage is calculated to be 50% or less, or 150% or more upon contact with the both of the ligand and the test substance is selected as a substance capable of regulating the signal transduction, on the basis of the radioactivity with the addition only of the ligand being 100% and the radioactivity without the addition of the ligand or the test substance being 0%.

Example 24

Assay of Activation of Signal Transduction Pathway Mediated by Gm1 Using Change in cAMP Level as Index $2 \times 10^5$ Cells of CHO cell were transfected with the dopamine D1 receptor expression vector (1 μg) obtained in Example 8 and the Gm1 expression vector obtained in Example 7 (pcDNA-Gm1; 3 μg) by a lipofection method to prepare a test cell.

Then, the cells were inoculated to each well of a 96-well plate at $3 \times 10^4$ cells/well, and cultured for about 24 hours. Then, the culture medium was removed, and 80 μl of 1 mM IBMX-supplemented OPTI-MEN (Invitrogen) was added to the cells, which were then incubated at 37° C. for 10 minutes.

Then, 10 μM of dopamine as a GPCR ligand was added and incubated at 37° C. for 30 minutes.

Then, the reaction buffer was removed, and the cAMP level was determined using a HitHunter ECF cyclic AMP chemiluminescent assay kit (Applied Biosystems). As a control, a test cell which had been brought into contact with nothing were examined for their cAMP levels in the similar manner.

Figure 6:
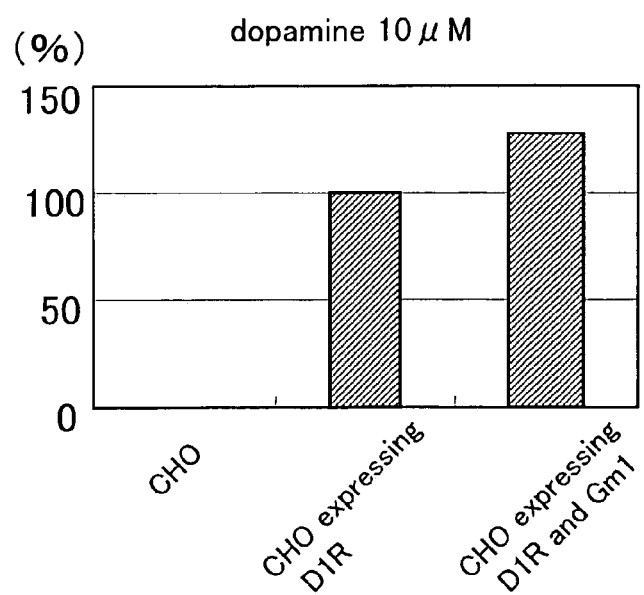
FIG. 6 is a schematic view indicating that dopamine caused a signal transduction mediated by the dopamine D1 receptor and the Gm1 (Example 24)

The cAMP level of the test cell expressing the Gm1 and the dopamine D1 receptor was determined on the basis of the cAMP level upon no contact being regarded to be 0% while the cAMP level of the control cell expressing only the dopamine D1 receptor being regarded to be 100%, and was revealed to be 127%. Therefore, it was proven that the Gm1-mediated signal transduction system do exist (FIG. 6).

Example 25

Assay of Activation of Signal Transduction Pathway Mediated by Gm1 Using Change in cAMP Level as Index $2 \times 10^5$ Cells of CHO cell were transfected with the adenosine A2a receptor expression vector (1 μg) obtained in Example 8 and the Gm1 expression vector obtained in Example 7 (pcDNA-Gm1; 3 μg) by a lipofection method to prepare a test cell.

Then, the cells were inoculated to each well of a 96-well plate at $3 \times 10^4$ cells/well, and cultured for about 24 hours. Then, the culture medium was removed, and 80 μl of 1 mM IBMX-supplemented OPTI-MEN (Invitrogen) was added to the cells, which were then incubated at 37° C. for 10 minutes.

Then, 10 μM of adenosine as a GPCR ligand was added and incubated at 37° C. for 30 minutes.

Then, the reaction buffer was removed, and the cAMP level was determined using a HitHunter ECF cyclic AMP chemiluminescent assay kit (Applied Biosystems). As a control, a test cell which had been brought into contact with nothing were examined for their cAMP levels in the similar manner.

Figure 7:
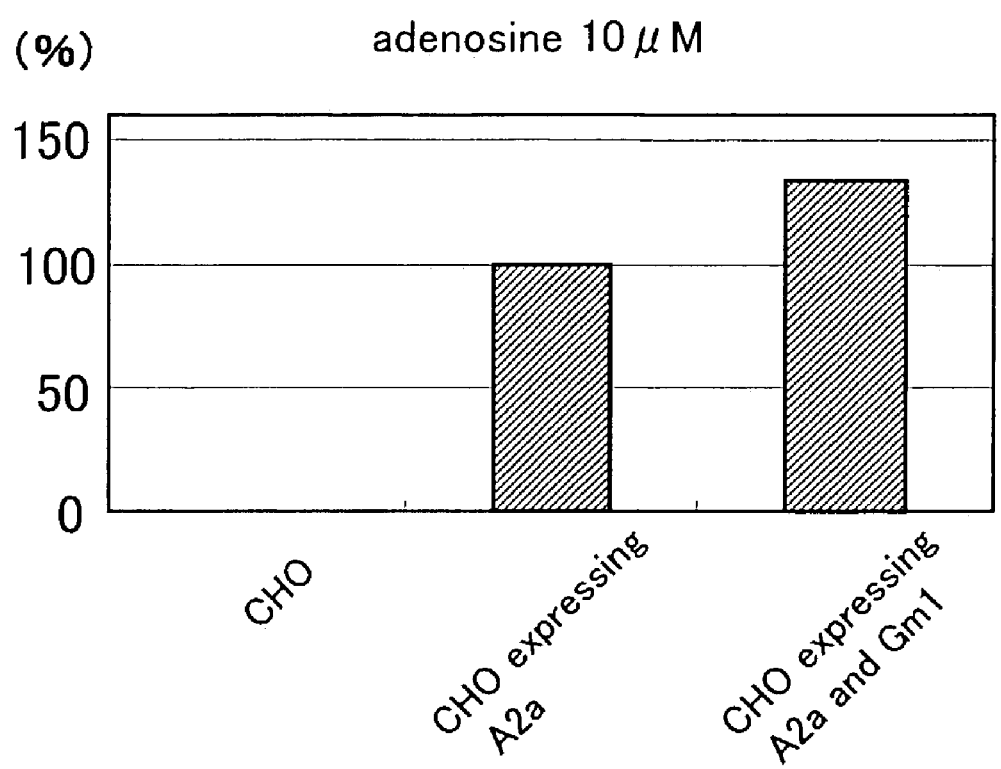
FIG. 7 is a schematic view indicating that adenosine caused a signal transduction mediated by the adenosine A2a receptor and the Gm1 (Example 24).

The cAMP level when allowing the Gm1 and the adenosine A2a receptor to be expressed was determined on the basis of the cAMP level upon no contact being regarded to be 0% while the cAMP level of the cell allowed to express only the adenosine A2a receptor being regarded to be 100%, and was revealed to be 134%. Therefore, it was proven that the Gm1-mediated signal transduction system do exist (FIG. 7).

Example 26

Cloning of Mouse Gm1 Protein-Encoding cDNA

A pDr-mGm1 which is a plasmid having a DNA encoding the full-length mouse Gm1 was produced as described below.

20 ng of a mouse brain-derived cDNA library (Clontech) was employed as a template together with 10 μm of a forward primer (5'-ATGGGCCTATGCTACAGCCTGCG-GCCGCT; SEQ ID No:29) and 10 μM of a reverse primer prmGm1STOP (5'-TCACAAGAGTTCGTACTGCT-TGAGATGCATTCT; SEQ ID No:30) as well as a TAKARA LA Taq polymerase (TAKARA LA Taq with GC Buffer, Takara) to conduct a PCR to obtain an amplified DNA.

The PCR condition involved 35 cycles, each cycle involving incubations at 95° C. for 30 seconds followed by 60° C. for 30 seconds followed by 72° C. for 2 minutes. The resultant DNA was subjected to an agarose gel electrophoresis followed by a purification with a QIAquick Gel Extraction kit (QIAGEN), and then recovered. This purified and recovered DNA was used as an insert DNA.

Then, a QIAGEN PCR Cloning kit (QIAGEN) was used following to its attached protocol to insert the insert DNA (50 ng) into a cloning site of a pDrive vector (25 ng), whereby producing a pDr-mGm1.

The DNA thus obtained was subjected to an ABI377DNA sequencer to determine the nucleotide sequence, which was revealed to contain the nucleotide Nos. 1 to 1347 in the nucleotide sequence represented by SEQ ID No:27 and to encode the full-length amino acid sequence represented by SEQ ID No:25.

Example 27

Cloning of Rat Gm1 Protein-Encoding cDNA

A pDr-rGm1 which is a plasmid having a DNA encoding the full-length rat Gm1 was produced as described below.

20 ng of a rat brain-derived cDNA library (Clontech) was employed as a template together with 10 μM of a forward primer prrGm1ATG (5'-ATGGGCCTGTGCTACAGC-CTACGGCCGCTG; SEQ ID No:31) and 10 μM of a reverse primer prrGm1'STOP (5'-TCACAAGAGTTCGTACTGCT-TGAGGTGCATTCT; SEQ ID No:32) as well as a TAKARA LA Taq polymerase (TAKARA LA Taq with GC Buffer, Takara) to conduct a PCR to obtain an amplified DNA.

The PCR condition involved 35 cycles, each cycle involving incubations at 95° C. for 30 seconds followed by 60° C. for 30 seconds followed by 72° C. for 2 minutes. The resultant DNA was subjected to an agarose gel electrophoresis followed by a purification with a QIAquick Gel Extraction kit (QIAGEN), and then recovered. This purified and recovered DNA was used as an insert DNA.

Then, a QIAGEN PCR Cloning kit (QIAGEN) was used following to its attached protocol to insert the insert DNA (50 ng) into a cloning site of a pDrive vector (25 ng), whereby producing a pDr-rGm1.

The DNA thus obtained was subjected to an ABI377DNA sequencer to determine the nucleotide sequence, which was revealed to contain the nucleotide Nos. 1 to 1353 in the nucleotide sequence represented by SEQ ID No:28 and to encode the full-length amino acid sequence represented by SEQ ID No:26.

Free Text in Sequence Listing
SEQ ID No:3
  an example of the ribozyme of the present invention
SEQ ID No:4
  an example of the ribozyme of the present invention
SEQ ID No:5
  an example of the ribozyme of the present invention
SEQ ID No:6
  an example of the ribozyme of the present invention
SEQ ID No:7
  an example of the ribozyme of the present invention
SEQ ID No:8
  an example of the ribozyme of the present invention
SEQ ID No:9
  an example of the oligonucleotide of the present invention
SEQ ID No:10
  an example of the oligonucleotide of the present invention
SEQ ID No:11
  a primer used in an example of the present invention
SEQ ID No:12
  a primer used in an example of the present invention
SEQ ID No:13
  a primer used in an example of the present invention
SEQ ID No:14
  a primer used in an example of the present invention
SEQ ID No:15
  a primer used in an example of the present invention
SEQ ID No:16
  a primer used in an example of the present invention
SEQ ID No:17
  a primer used in an example of the present invention
SEQ ID No:18
  a primer used in an example of the present invention
SEQ ID No:19
  a primer used in an example of the present invention
SEQ ID No:20
  a primer used in an example of the present invention
SEQ ID No:21
  a primer used in an example of the present invention
SEQ ID No:22
  a primer used in an example of the present invention
SEQ ID No:23
  a primer used in an example of the present invention
SEQ ID No:24
  a primer used in an example of the present invention
SEQ ID No:29
  a primer used in an example of the present invention
SEQ ID No:30
  a primer used in an example of the present invention
SEQ ID No:31
  a primer used in an example of the present invention
SEQ ID No:32
  a primer used in an example of the present invention
SEQ ID No:33
  a primer used in an example of the present invention
SEQ ID No:34
  a primer used in an example of the present invention

---

What is claimed is:

1. An isolated polynucleotide comprising a nucleotide sequence selected from the group consisting of:
   (a) a nucleotide sequence encoding the amino acid sequence represented by SEQ ID NO:1;
   (b) a nucleotide sequence encoding an amino acid sequence of a protein involved in a G protein-coupled receptor mediated signal transduction, wherein said protein has an ability to mediate a signal transduction from a dopamine D1 receptor or an adenosine A2a receptor to an adenylate cyclase, and wherein said amino acid sequence has a homology of 85% or more with the amino acid sequence of SEQ ID NO:1, and retains amino acid sequences represented by amino acid residues 119 to 133, 287 to 292, 353 to 359, and 428 to 435 in the amino acid sequence of SEQ ID NO:1;
   (c) a nucleotide sequence encoding the amino acid sequence represented by SEQ ID NO:25;
   (d) a nucleotide sequence encoding the amino acid sequence represented by SEQ ID NO:26;
   (e) the nucleotide sequence represented by SEQ ID NO:2;
   (f) the nucleotide sequence represented by SEQ ID NO:27; and
   (g) the nucleotide sequence represented by SEQ ID NO:28.

2. A recombinant vector containing a polynucleotide according to claim 1.

3. A method for producing a transformant comprising a step for transducing a recombinant vector according to claim 2 into an isolated host cell.

4. A method for screening for a substance capable of regulating a signal transduction mediated by a G protein-coupled receptor and a G protein comprising:
   (a) bringing a test substance into contact with a test cell having a recombinant vector according to claim 2 and a recombinant vector containing a DNA encoding a G protein-coupled receptor protein;

(b) measuring G protein effector activity or an index value correlating therewith in the test cell; and
(c) comparing this effector activity or the index value correlating therewith with effector activity or an index value correlating therewith in a test cell which has not been brought into contact with the test substance, to thereby select a test substance capable of altering the effector activity or the index value correlating therewith in the test cell.

5. A method for screening for a substance capable of regulating a signal transduction mediated by a G protein-coupled receptor and a G protein comprising:
(a) bringing a test substance into contact with a test cell having a recombinant vector according to claim 2 and a recombinant vector containing a DNA encoding a G protein-coupled receptor protein;
(b) measuring G protein effector activity or an index value correlating therewith in the test cell; and
(c) comparing this effector activity with effector activity or an index value correlating therewith when the test substance has been brought into contact with a control cell having no recombinant vector according to claim 2 but having a recombinant vector containing a DNA encoding a G protein-coupled receptor protein, to thereby select a test substance causing a difference in the effector activity or the index value correlating therewith between the test cell and the control cell.

6. A method for screening for a substance capable of regulating a signal transduction mediated by a G protein-coupled receptor and a G protein comprising:
(a) bringing a test substance into contact with a test cell having a recombinant vector according to claim 2 and a recombinant vector containing a DNA encoding a G protein-coupled receptor protein;
(b) measuring G protein effector activity or an index value correlating therewith in the test cell; and
(c) comparing this effector activity or the index value correlating therewith with effector activity or an index value correlating therewith when the test substance has been brought into contact with a control cell having no recombinant vector containing a DNA encoding a G protein-coupled receptor protein but having a recombinant vector according to claim 2, to thereby select a test substance causing a difference in the effector activity or the index value correlating therewith between the test cell and the control cell.

7. A method for screening for a substance capable of regulating a signal transduction mediated by a G protein-coupled receptor and a G protein comprising:
(a) bringing a test substance and a G protein-coupled receptor ligand into contact with a test cell having a recombinant vector according to claim 2 and a recombinant vector containing a DNA encoding a G protein-coupled receptor protein;
(b) measuring G protein effector activity or an index value correlating therewith in the test cell; and
(c) comparing this effector activity or the index value correlating therewith with effector activity or an index value correlating therewith in a test cell which has not been brought into contact with the test substance but has been brought into contact with the ligand, to thereby select a test substance capable of altering the effector activity or the index value correlating therewith in the test cell.

8. A method for screening for a substance capable of regulating a signal transduction mediated by a G protein-coupled receptor and a G protein comprising:
(a) bringing a test substance and a G protein-coupled receptor ligand into contact with a test cell having a recombinant vector according to claim 2 and a recombinant vector containing a DNA encoding a G protein-coupled receptor protein;
(b) measuring G protein effector activity or an index value correlating therewith in the test cell;
(c) comparing this effector activity with effector activity in a test cell which has not been brought into contact with the test substance but has been brought into contact with the ligand, whereby investigating change in the effector activity in the test cell; and
(d) comparing a rate of change in this effector activity or the index value correlating therewith with a rate of change in effector activity or an index value correlating therewith when the test substance and the ligand has been brought into contact with a control cell having no recombinant vector containing a DNA encoding a G protein-coupled receptor protein but having a recombinant vector according to claim 2, to thereby select a test substance causing a difference in the rate of change in the effector activity or the index value correlating therewith between the test cell and the control cell.

9. A method for producing a recombinant vector comprising a step for integrating a polynucleotide according to claim 1 into a vector capable of being replicated in a host cell.

10. A transformant having a recombinant vector according to claim 2.

11. A method for producing a G protein α-subunit comprising culturing a transformant having a recombinant vector containing a polynucleotide according to claim 1 and recovering from the culture a protein resulting from the polynucleotide according to claim 1.

12. An agent for regulating a G protein-coupled receptor mediated signal transduction containing as an active ingredient a polynucleotide according to claim 1.

13. A method for screening for a substance capable of regulating a signal transduction mediated by a G protein-coupled receptor and a G protein comprising:
(a) culturing a transformant having a recombinant vector containing a polynucleotide according to claim 1 and preparing from the cultured transformant a cell membrane fraction that contains a protein encoded by the polynucleotide according to claim 1;
(b) bringing a test substance into contact with the cell membrane fraction prepared in (a) and a cell membrane fraction of a cell having a recombinant vector containing a DNA encoding a G protein-coupled receptor;
(c) assaying a level of the binding of GTP to the cell membrane fractions; and
(d) comparing the assayed level of this GTP binding with an assayed level of GTP binding to cell membrane fractions which have not been brought into contact with the test substance, to thereby select a test substance capable of altering the assayed level of the GTP binding to the cell membrane fractions.

14. A method for screening for a substance capable of regulating a signal transduction mediated by a G protein-coupled receptor and a G protein comprising:
(a) culturing a transformant having a recombinant vector containing a polynucleotide according to claim 1 and preparing from the cultured transformant a cell membrane fraction that contains a protein encoded by the polynucleotide according to claim 1;
(b) bringing a test substance and a G protein-coupled receptor ligand into contact with the cell membrane fraction prepared in (a) and a cell membrane fraction of a cell having a recombinant vector containing a DNA encoding a G protein-coupled receptor;

(c) assaying a level of binding of GTP to the cell membrane fractions; and (d) comparing the assayed level of GTP binding from (c) with an assayed level of GTP binding to cell membrane fractions which have not been brought into contact with the test substance but have been brought into contact with the ligand, to thereby select a test substance capable of altering the assayed level of the GTP binding to the cell membrane fractions.

15. A method for screening for a substance capable of regulating a signal transduction mediated by a G protein-coupled receptor and a G protein comprising:

(a) culturing a transformant having a recombinant vector containing a polynucleotide according to claim 1 and a recombinant vector containing a polynucleotide encoding a G protein-coupled receptor, and preparing from the cultured transformant a cell membrane fraction that contains a protein encoded by the polynucleotide according to claim and the G protein-coupled receptor;

(b) bringing a test substance into contact with the cell membrane fraction prepared in (a);

(c) assaying a level of binding of GTP to the cell membrane fraction; and (d) comparing the level of binding of GTP assayed from (c) with a level of binding of GTP to a cell membrane fraction which has not been brought into contact with the test substance, to whereby select a test substance capable of altering the level of binding of GTP to the cell membrane fraction.

16. A method for screening for a substance capable of regulating a signal transduction mediated by a G protein-coupled receptor and a G protein comprising:

(a) culturing a transformant having a recombinant vector containing a polynucleotide according to claim 1 and a recombinant vector containing a polynucleotide encoding a G protein-coupled receptor, and preparing from the cultured transformant a cell membrane fraction that contains a protein encoded by the polynucleotide according to claim 1 and the G protein-coupled receptor;

(b) bringing a test substance and a G protein-coupled receptor ligand into contact with the cell membrane fraction prepared in (a);

(c) assaying a level of binding of GTP to the cell membrane fraction; and (d) comparing the level of binding of GTP assayed from (c) with a level of binding of GTP to a cell membrane fraction prepared which has not been brought into contact with the test substance but has been brought into contact with the ligand, to whereby select a test substance capable of altering the level of binding of GTP to the cell membrane fraction.

17. A polynucleotide consisting of the nucleotide sequence represented by SEQ ID NO:2.

18. A polynucleotide consisting of the nucleotide sequence represented by SEQ ID NO:27.

19. A polynucleotide consisting of the nucleotide sequence represented by SEQ ID NO:28.

* * * * *